(12) United States Patent
Kostrzewski et al.

(10) Patent No.: US 11,103,316 B2
(45) Date of Patent: Aug. 31, 2021

(54) ROBOT ASSISTED VOLUME REMOVAL DURING SURGERY

(71) Applicant: KB Medical SA, Lausanne (CH)

(72) Inventors: Szymon Kostrzewski, Lausanne (CH); Chetan Patel, Altamonte Springs, FL (US); Alexander Mason, Boulder, CO (US)

(73) Assignee: Globus Medical Inc., Audubon, PA (US)

( * ) Notice: Subject to any disclaimer, the term of this patent is extended or adjusted under 35 U.S.C. 154(b) by 1136 days.

(21) Appl. No.: 14/957,204

(22) Filed: Dec. 2, 2015

(65) Prior Publication Data

US 2016/0151120 A1   Jun. 2, 2016

Related U.S. Application Data

(60) Provisional application No. 62/086,677, filed on Dec. 2, 2014.

(51) Int. Cl.
*A61B 34/00* (2016.01)
*A61B 34/30* (2016.01)
(Continued)

(52) U.S. Cl.
CPC .......... *A61B 34/30* (2016.02); *A61B 17/1671* (2013.01); *A61B 17/3403* (2013.01);
(Continued)

(58) Field of Classification Search
None
See application file for complete search history.

(56) References Cited

U.S. PATENT DOCUMENTS

| 4,150,293 A | 4/1979 | Franke |
| 4,166,602 A | 9/1979 | Nilsen et al. |

(Continued)

FOREIGN PATENT DOCUMENTS

| DE | 10003051 A1 | 8/2001 |
| EP | 1693011 A1 | 8/2006 |

(Continued)

OTHER PUBLICATIONS

Rosa Is a New Stereotactic Neurological Surgery Robot, Neurological Surgery, Jun. 13, 2011 (http://www.medgadget.com/2011/06/rosa-neuro-surgery-robot.html).

(Continued)

*Primary Examiner* — Rex R Holmes
*Assistant Examiner* — Sana Sahand

(57) ABSTRACT

Described herein is a device and method used to effectively remove volume inside a patient in various types of surgeries, such as spinal surgeries (e.g. laminotomy), neurosurgeries (various types of craniotomy), ENT surgeries (e.g. tumor removal), and orthopedic surgeries (bone removal). Robotic assistance linked with a navigation system and medical imaging it can shorten surgery time, make the surgery safer and free surgeon from doing repetitive and laborious tasks. In certain embodiments, the disclosed technology includes a surgical instrument holder for use with a robotic surgical system. In certain embodiments, the surgical instrument holder is attached to or is part of an end effector of a robotic arm, and provides a rigid structure that allows for precise removal of a target volume in a patient.

19 Claims, 22 Drawing Sheets

(51) Int. Cl.
*A61B 17/16* (2006.01)
*A61B 17/00* (2006.01)
*A61B 90/00* (2016.01)
*A61B 17/34* (2006.01)

(52) U.S. Cl.
CPC .............. *A61B 2017/00017* (2013.01); *A61B 2017/00477* (2013.01); *A61B 2090/064* (2016.02); *A61B 2576/00* (2013.01)

(56) References Cited

U.S. PATENT DOCUMENTS

| | | | |
|---|---|---|---|
| 4,799,779 | A | 1/1989 | Mesmer |
| 5,246,010 | A | 9/1993 | Gazzara et al. |
| 5,408,409 | A | 4/1995 | Glassman et al. |
| 5,598,453 | A | 1/1997 | Baba et al. |
| 5,772,594 | A | 6/1998 | Barrick |
| 5,810,880 | A | 9/1998 | Jensen et al. |
| 5,948,002 | A | 9/1999 | Bonutti |
| 5,987,960 | A | 11/1999 | Messner et al. |
| 6,031,888 | A | 2/2000 | Ivan et al. |
| 6,132,368 | A | 10/2000 | Cooper |
| 6,144,875 | A | 11/2000 | Schweikard et al. |
| D435,107 | S | 12/2000 | Blair et al. |
| 6,203,196 | B1 | 3/2001 | Meyer et al. |
| 6,306,126 | B1 | 10/2001 | Montezuma |
| 6,314,311 | B1 | 11/2001 | Williams et al. |
| 6,320,929 | B1 | 11/2001 | Von Der Haar |
| D456,080 | S | 4/2002 | Karlsson |
| D461,484 | S | 8/2002 | Kraft |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,475 | B1 | 12/2002 | Seeley et al. |
| 6,501,981 | B1 | 12/2002 | Schweikard et al. |
| 6,535,756 | B1 | 3/2003 | Simon et al. |
| 6,604,021 | B2 | 8/2003 | Imai et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,666,579 | B2 | 12/2003 | Jensen |
| 6,757,068 | B2 | 6/2004 | Foxlin |
| 6,782,287 | B2 | 8/2004 | Grzeszczuk et al. |
| 6,856,826 | B2 | 2/2005 | Seeley et al. |
| 6,856,827 | B2 | 2/2005 | Seeley et al. |
| D506,257 | S | 6/2005 | Smith |
| 6,920,347 | B2 | 7/2005 | Simon et al. |
| 6,922,632 | B2 | 7/2005 | Foxlin |
| 6,988,009 | B2 | 1/2006 | Grimm et al. |
| 6,996,487 | B2 | 2/2006 | Jutras et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,099,428 | B2 | 8/2006 | Clinthorne et al. |
| D528,216 | S | 9/2006 | Korner |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,155,316 | B2 | 12/2006 | Sutherland et al. |
| 7,194,120 | B2 | 3/2007 | Wicker et al. |
| 7,196,454 | B2 | 3/2007 | Baur et al. |
| 7,197,107 | B2 | 3/2007 | Arai et al. |
| 7,231,014 | B2 | 6/2007 | Levy |
| 7,231,063 | B2 | 6/2007 | Naimark et al. |
| D548,759 | S | 8/2007 | Kraft |
| D553,655 | S | 10/2007 | Jennings et al. |
| 7,301,648 | B2 | 11/2007 | Foxlin |
| 7,313,430 | B2 | 12/2007 | Urquhart et al. |
| 7,318,805 | B2 | 1/2008 | Schweikard et al. |
| 7,324,623 | B2 | 1/2008 | Heuscher et al. |
| 7,327,865 | B2 | 2/2008 | Fu et al. |
| D572,739 | S | 7/2008 | Jennings et al. |
| 7,460,637 | B2 | 12/2008 | Clinthorne et al. |
| 7,493,153 | B2 | 2/2009 | Ahmed et al. |
| 7,505,617 | B2 | 3/2009 | Fu et al. |
| 7,623,902 | B2 | 11/2009 | Pacheco |
| 7,643,862 | B2 | 1/2010 | Schoenefeld |
| 7,661,881 | B2 | 2/2010 | Gregerson et al. |
| 7,683,331 | B2 | 3/2010 | Chang |
| 7,683,332 | B2 | 3/2010 | Chang |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,725,253 | B2 | 5/2010 | Foxlin |
| 7,726,171 | B2 | 6/2010 | Langlotz et al. |
| 7,760,849 | B2 | 7/2010 | Zhang |
| 7,796,728 | B2 | 9/2010 | Bergfjord |
| 7,813,838 | B2 | 10/2010 | Sommer |
| 7,835,778 | B2 | 11/2010 | Foley et al. |
| 7,835,784 | B2 | 11/2010 | Mire et al. |
| 7,840,256 | B2 | 11/2010 | Lakin et al. |
| 7,844,320 | B2 | 11/2010 | Shahidi |
| 7,853,305 | B2 | 12/2010 | Simon et al. |
| 7,853,313 | B2 | 12/2010 | Thompson |
| 7,900,524 | B2 | 3/2011 | Calloway et al. |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 8,019,045 | B2 | 9/2011 | Kato |
| 8,021,310 | B2 | 9/2011 | Sanborn et al. |
| D646,703 | S | 10/2011 | Wong |
| 8,052,688 | B2 | 11/2011 | Wolf, II |
| 8,086,299 | B2 | 12/2011 | Adler et al. |
| 8,098,914 | B2 | 1/2012 | Liao et al. |
| 8,100,950 | B2 | 1/2012 | St. Clair et al. |
| D654,503 | S | 2/2012 | Sapper |
| 8,116,430 | B1 | 2/2012 | Shapiro et al. |
| 8,121,249 | B2 | 2/2012 | Wang et al. |
| D655,324 | S | 3/2012 | Wong |
| 8,150,494 | B2 | 4/2012 | Simon et al. |
| D660,845 | S | 5/2012 | Schmauch et al. |
| 8,208,708 | B2 | 6/2012 | Homan et al. |
| 8,224,024 | B2 | 7/2012 | Foxlin et al. |
| 8,273,076 | B2* | 9/2012 | Devengenzo .......... A61B 34/30 606/1 |
| 8,311,611 | B2 | 11/2012 | Csavoy et al. |
| 8,335,557 | B2 | 12/2012 | Maschke |
| 8,358,818 | B2 | 1/2013 | Miga et al. |
| 8,379,791 | B2 | 2/2013 | Forthmann et al. |
| 8,386,019 | B2 | 2/2013 | Camus et al. |
| D679,016 | S | 3/2013 | Jarva |
| 8,394,099 | B2 | 3/2013 | Patwardhan |
| 8,462,911 | B2 | 6/2013 | Vesel et al. |
| D685,479 | S | 7/2013 | Charles |
| 8,509,503 | B2 | 8/2013 | Nahum et al. |
| D690,421 | S | 9/2013 | Charles |
| 8,526,700 | B2 | 9/2013 | Isaacs |
| 8,541,970 | B2 | 9/2013 | Nowlin et al. |
| D692,139 | S | 10/2013 | Charles |
| 8,560,118 | B2 | 10/2013 | Green et al. |
| 8,597,198 | B2 | 12/2013 | Sanborn et al. |
| 8,611,985 | B2 | 12/2013 | Lavallee et al. |
| 8,630,389 | B2 | 1/2014 | Kato |
| 8,634,897 | B2 | 1/2014 | Simon et al. |
| 8,660,635 | B2 | 2/2014 | Simon et al. |
| 8,678,647 | B2 | 3/2014 | Gregerson et al. |
| D702,841 | S | 4/2014 | Wyrozub |
| 8,696,458 | B2 | 4/2014 | Foxlin et al. |
| 8,706,185 | B2 | 4/2014 | Foley et al. |
| 8,727,618 | B2 | 5/2014 | Maschke et al. |
| 8,738,115 | B2 | 5/2014 | Amberg et al. |
| 8,740,882 | B2 | 6/2014 | Jun et al. |
| D708,332 | S | 7/2014 | Kim |
| 8,781,186 | B2 | 7/2014 | Clements et al. |
| 8,781,630 | B2 | 7/2014 | Banks et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,812,077 | B2 | 8/2014 | Dempsey |
| 8,814,793 | B2 | 8/2014 | Brabrand |
| 8,818,105 | B2 | 8/2014 | Myronenko et al. |

(56) References Cited

U.S. PATENT DOCUMENTS

| | | |
|---|---|---|
| 8,821,511 B2 | 9/2014 | Von Jako et al. |
| 8,867,703 B2 | 10/2014 | Shapiro et al. |
| 8,888,821 B2 | 11/2014 | Rezach et al. |
| 8,964,934 B2 | 2/2015 | Ein-Gal |
| D724,738 S | 3/2015 | Dorris et al. |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,125,680 B2 | 9/2015 | Kostrzewski et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2003/0097060 A1 | 5/2003 | Yanof et al. |
| 2004/0034282 A1 | 2/2004 | Quaid |
| 2004/0076259 A1 | 4/2004 | Jensen et al. |
| 2004/0128026 A1 | 7/2004 | Harris et al. |
| 2004/0143168 A1 | 7/2004 | Hu et al. |
| 2005/0245817 A1 | 11/2005 | Clayton et al. |
| 2006/0036264 A1 | 2/2006 | Selover et al. |
| 2006/0142657 A1 | 6/2006 | Quaid et al. |
| 2006/0161136 A1 | 7/2006 | Anderson et al. |
| 2006/0161138 A1 | 7/2006 | Orban et al. |
| 2006/0184396 A1 | 8/2006 | Dennis et al. |
| 2006/0291612 A1 | 12/2006 | Nishide et al. |
| 2007/0005189 A1 | 1/2007 | Furubo |
| 2007/0032906 A1 | 2/2007 | Sutherland et al. |
| 2007/0038059 A1 | 2/2007 | Sheffer et al. |
| 2007/0055291 A1* | 3/2007 | Birkmeyer ............ A61B 90/13 606/130 |
| 2007/0073133 A1 | 3/2007 | Schoenefeld |
| 2007/0119123 A1 | 5/2007 | Clark et al. |
| 2007/0119274 A1* | 5/2007 | Devengenzo ............ B25J 15/04 74/490.01 |
| 2007/0156157 A1 | 7/2007 | Nahum et al. |
| 2007/0239187 A1* | 10/2007 | Brunnett ............ A61B 17/1622 606/172 |
| 2007/0270685 A1 | 11/2007 | Kang et al. |
| 2008/0004523 A1 | 1/2008 | Jensen |
| 2008/0010706 A1 | 1/2008 | Moses et al. |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0147089 A1 | 6/2008 | Loh et al. |
| 2008/0161680 A1 | 7/2008 | Von Jako et al. |
| 2008/0215181 A1 | 9/2008 | Smith et al. |
| 2008/0221520 A1 | 9/2008 | Nagel et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0287862 A1 | 11/2008 | Weitzner et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0088848 A1 | 4/2009 | Martz et al. |
| 2009/0185655 A1 | 7/2009 | Koken et al. |
| 2009/0198121 A1 | 8/2009 | Hoheisel |
| 2009/0245956 A1* | 10/2009 | Apkarian ............ A61B 17/1626 408/1 R |
| 2009/0326318 A1 | 12/2009 | Tognaccini et al. |
| 2010/0022874 A1 | 1/2010 | Wang et al. |
| 2010/0030233 A1* | 2/2010 | Whitman ............... A61B 34/30 606/130 |
| 2010/0039506 A1 | 2/2010 | Sarvestani et al. |
| 2010/0125286 A1 | 5/2010 | Wang et al. |
| 2010/0166496 A1 | 7/2010 | Bennett et al. |
| 2010/0192720 A1 | 8/2010 | Helmer et al. |
| 2010/0210939 A1 | 8/2010 | Hartmann et al. |
| 2010/0228117 A1 | 9/2010 | Hartmann |
| 2010/0274120 A1 | 10/2010 | Heuscher |
| 2010/0319713 A1 | 12/2010 | Byers et al. |
| 2011/0082462 A1 | 4/2011 | Suarez et al. |
| 2011/0087238 A1 | 4/2011 | Wang et al. |
| 2011/0098553 A1 | 4/2011 | Robbins et al. |
| 2011/0126844 A1 | 6/2011 | Cinquin et al. |
| 2011/0130761 A1 | 6/2011 | Plaskos et al. |
| 2011/0190789 A1 | 8/2011 | Thiran et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0059378 A1 | 3/2012 | Farrell |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2013/0016889 A1 | 1/2013 | Myronenko et al. |
| 2013/0041219 A1* | 2/2013 | Hasegawa ............ A61B 34/76 600/109 |
| 2013/0060146 A1 | 3/2013 | Yang et al. |
| 2013/0081636 A1 | 4/2013 | Schuele |
| 2013/0094742 A1 | 4/2013 | Feilkas |
| 2013/0113791 A1 | 5/2013 | Isaacs et al. |
| 2013/0113798 A1 | 5/2013 | Nahum et al. |
| 2013/0165937 A1 | 6/2013 | Patwardhan |
| 2013/0172902 A1 | 7/2013 | Lightcap et al. |
| 2013/0281821 A1 | 10/2013 | Liu et al. |
| 2013/0307955 A1 | 11/2013 | Deitz et al. |
| 2013/0317344 A1 | 11/2013 | Borus et al. |
| 2013/0342578 A1 | 12/2013 | Isaacs |
| 2013/0345757 A1 | 12/2013 | Stad |
| 2014/0039519 A1 | 2/2014 | Inoue et al. |
| 2014/0046132 A1 | 2/2014 | Hoeg et al. |
| 2014/0049629 A1 | 2/2014 | Siewerdsen et al. |
| 2014/0052151 A1 | 2/2014 | Hingwe et al. |
| 2014/0066944 A1* | 3/2014 | Taylor ................. B25J 15/0466 606/103 |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0213848 A1* | 7/2014 | Moskowitz ...... A61B 17/00234 600/106 |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0275955 A1 | 9/2014 | Crawford et al. |
| 2014/0371577 A1 | 12/2014 | Mallet et al. |
| 2015/0032164 A1 | 1/2015 | Crawford et al. |
| 2015/0039034 A1 | 2/2015 | Frankel et al. |
| 2015/0045764 A1 | 2/2015 | Kaplan et al. |
| 2015/0045813 A1 | 2/2015 | Kostrzewski et al. |
| 2015/0085970 A1 | 3/2015 | Bouhnik et al. |
| 2015/0100066 A1 | 4/2015 | Kostrzewski et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1 | 7/2015 | Kostrzewski et al. |
| 2015/0202009 A1 | 7/2015 | Nussbaumer et al. |
| 2015/0213633 A1 | 7/2015 | Chang et al. |

(56) References Cited

U.S. PATENT DOCUMENTS

| | | |
|---|---|---|
| 2015/0223897 A1 | 8/2015 | Kostrzewski et al. |
| 2015/0305817 A1 | 10/2015 | Kostrzewski |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | | |
|---|---|---|---|
| JP | 2002500524 | 1/2002 | |
| JP | 2009537229 A | 10/2009 | |
| JP | 2012235936 A | 12/2012 | |
| WO | WO-98/02107 A1 | 1/1998 | |
| WO | 9825666 A1 | 6/1998 | |
| WO | WO-2004/014244 A2 | 2/2004 | |
| WO | WO-2005/122916 A1 | 12/2005 | |
| WO | WO-2006/091494 A1 | 8/2006 | |
| WO | WO-2007/136768 A2 | 11/2007 | |
| WO | WO-2007136768 A2 * | 11/2007 | ............. A61B 34/20 |
| WO | WO-2008/097540 A2 | 8/2008 | |
| WO | WO-2009/013406 A2 | 1/2009 | |
| WO | WO-2012/131660 A1 | 10/2012 | |
| WO | WO-2012/133912 A1 | 10/2012 | |
| WO | WO-2013/079843 A1 | 6/2013 | |
| WO | WO-2013/098496 A1 | 7/2013 | |
| WO | WO-2013/160239 A1 | 10/2013 | |
| WO | WO-2013/192598 A1 | 12/2013 | |
| WO | WO-2015/049109 A1 | 4/2015 | |
| WO | WO-2015/107099 A1 | 7/2015 | |
| WO | WO-2015/110542 A1 | 7/2015 | |
| WO | WO-2015/121311 A1 | 8/2015 | |
| WO | WO-2015/162256 A1 | 10/2015 | |

OTHER PUBLICATIONS

Zemiti, N. et al., A new Robot for Force Control in Minimally Invasive Surgery, Proceedings of 2004 IEEE/RSJ International Conference on Intelligent Robots and Systems, 4:3643-3648 (2004).

* cited by examiner

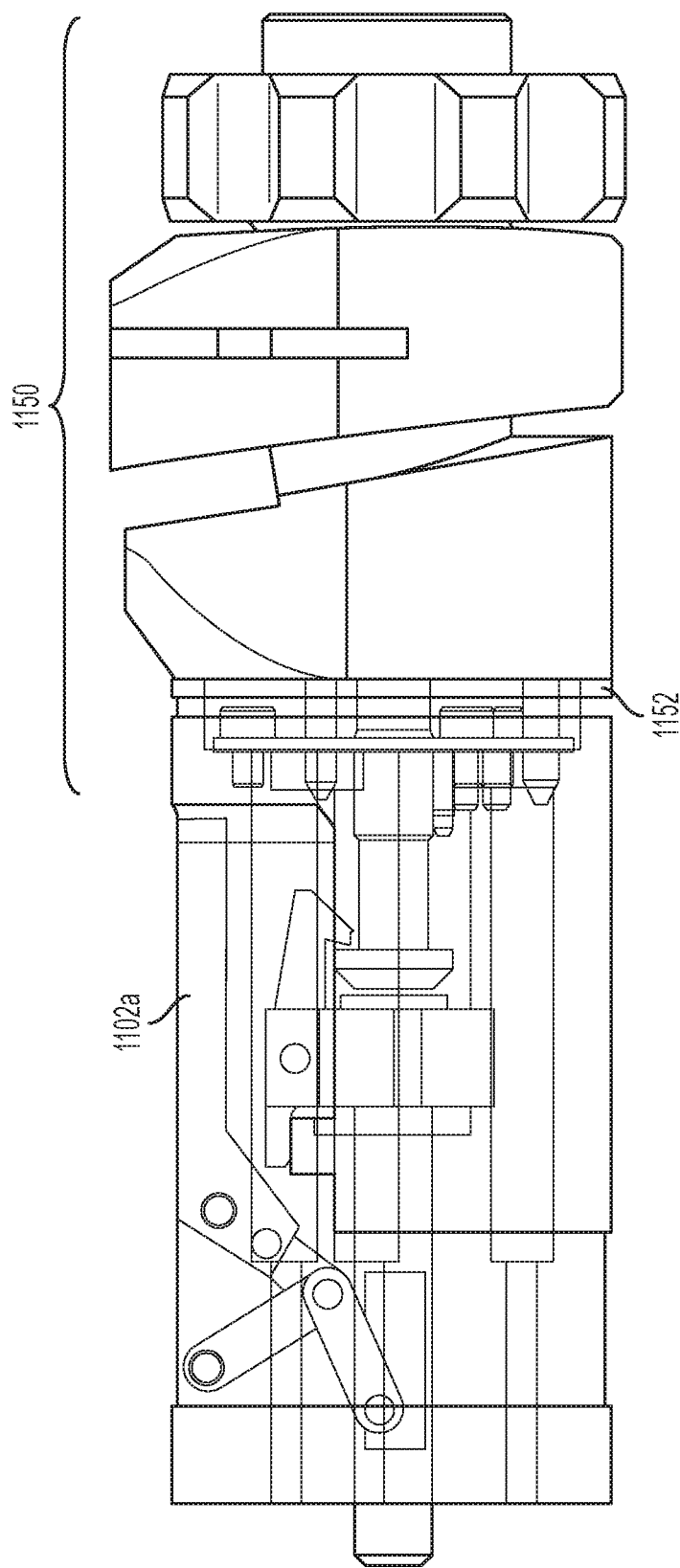

ROBOT ASSISTED VOLUME REMOVAL DURING SURGERY

PRIORITY APPLICATION

This application claims priority to U.S. Provisional Patent Application No. 62/086,677, filed Dec. 2, 2014, titled "Robot Assisted Volume Removal During Surgery", the content of which is expressly incorporated by reference herein in its entirety.

BACKGROUND OF THE INVENTION

Spinal stenosis (narrowing of the spinal canal) is the single most common diagnosis that leads to spinal surgery. A laminotomy may be performed to alleviate pain associated with spinal stenosis by partially removing/trimming the vertebra lamina shown in FIG. 1, thereby decompressing the corresponding spinal cord and/or spinal nerve root. During this type of surgery, after obtaining access to the vertebrae, a surgeon manually removes portions of the lamina. The surgical instruments used for this task include surgical pliers and a high-speed burr as shown in FIGS. 2A and 2B, respectively.

Removal/trimming of the lamina is a difficult process. The surgeon must be particularly careful not to damage spinal dura mater (tissue protecting spinal cord) which would lead to serious complications. This is a lengthy process which may take around 20 min per vertebra (e.g., 60 minutes for three vertebra). Furthermore, removing bony tissue requires repetitive movements which are tiring and may lead to repetitive motion disorders for surgeons performing these surgeries daily.

SUMMARY OF THE INVENTION

Described herein is a device and method used to effectively remove volume inside a patient in various types of surgeries, such as spinal surgeries (e.g. laminotomy), neurosurgeries (various types of craniotomy), ENT surgeries (e.g. tumor removal), and orthopedic surgeries (bone removal). The disclosed technology provides robotic assistance linked with a navigation system and medical imaging to shorten surgery time, make the surgery safer and free surgeons from doing repetitive and laborious tasks. The disclosed technology is also compatible with robotic surgical system described in U.S. patent application Ser. No. 14/266,769, filed Apr. 30, 2014, and entitled "Apparatus, Systems, and Methods for Precise Guidance of Surgical Tool" which is hereby incorporated by reference in its entirety, thereby, for example, allowing the same robotic surgical system to assist with different aspects of spinal surgery.

In certain embodiments, the disclosed technology includes a surgical instrument holder for use with a robotic surgical system. In certain embodiments, the holder is attached to or is part of an end effector of a robotic arm, and provides a rigid structure that can be used with a surgical tool to affect precise removal of a target volume in a patient.

In certain embodiments, the holder has a tubular shape with a longitudinal notch along a portion of its length. The holder is sized to allow a surgical instrument to slide through the holder in a fixed orientation while the holder is held by the robotic arm. The surgical instrument, in certain embodiments, is fitted with a tool support having a peg sized to fit the notch. A navigational marker (e.g., a multipoint, planar marker) may be attached thereto via the peg. Thus, because of the notch, movement of the surgical instrument is constrained in a fixed orientation as it slides along the axis defined by the holder. When a navigation marker is coupled to the peg, the navigation marker can be tracked (e.g., and hence the location of a surgical instrument connected to the navigation marker) when the surgical instrument is fully inserted and secured in the holder (e.g., in part by a locking mechanism). This facilitates and simplifies tracking of the marker, for example, via a remote tracking system that displays real-time tracking of the surgical instrument during the surgical procedure.

The disclosed technology, in certain embodiments, includes an instrument holder with a rigid hollow tubular structure having a proximal open end and a distal open end, said structure defining an axis along which movement of a surgical instrument sliding through the structure is restricted, wherein the tubular structure has an interior surface shaped and sized to accommodate the surgical instrument sliding through the surgical instrument holder such that movement of the surgical instrument is constrained to move along the axis defined by the surgical instrument holder (e.g., thereby allowing rapid exchange of surgical instruments held by the surgical instrument holder); and a connector element associated with (e.g., attached to) the holder that, when engaged (e.g., mated with) a corresponding connector element associated with a surgical instrument, provides power to the surgical instrument (e.g., and receives measurement information from a force sensor in the surgical instrument).

In certain embodiments, the tubular structure has an exterior surface including at least one flange that is sized and shaped to secure coupling of the surgical instrument holder to an end effector of the robotic surgical system.

In certain embodiments, the tubular structure includes a longitudinal notch along its length, wherein the longitudinal notch (e.g., slot) is sized in relation to a peg on (e.g., directly or indirectly) the surgical instrument to permit the surgical instrument to slide along the axis defined by the surgical instrument holder. In certain embodiments, the longitudinal notch is sized in relation to a peg to (i) permit a navigation marker attached to the surgical instrument at least in part via the peg to be viewable by a navigation camera along an entire range of movement of the surgical instrument through the surgical instrument holder, and (ii) constrain movement of the marker in a fixed orientation along the axis defined by the surgical instrument holder. In certain embodiments, navigation marker is used by navigation camera to track the surgical instrument.

In certain embodiments, a lock that, when engaged, restricts (e.g., prevents) movement of a surgical instrument within the rigid hollow tubular structure (e.g., such that the surgical instrument is constrained within the tubular structure in all directions). In certain embodiments, the lock, when engaged, prevents removal of the surgical instrument from the surgical instrument holder.

In certain embodiments, a force sensor that measures one or more forces and/or torques (e.g., 1 to 3 forces and 1 to 3 torques) applied to at least a portion of the surgical instrument. In certain embodiments, the surgical instrument includes a force sensor that measures one or more forces and/or torques (e.g., 1 to 3 forces and 1 to 3 torques) applied to at least a portion of the surgical instrument, and the measurement information provided to the surgical instrument holder via the connector comprises the one or more forces and/or torques.

In certain embodiments, the surgical instrument is a drill (e.g., with a drill bit). In some implementations, the portion of the surgical instrument to which the one or more forces and/or torques are applied is the drill bit. In certain embodiments, the surgical instrument is a drill (e.g., for preparing a hole for receiving a screw). In certain embodiments, the surgical instrument is a milling device, shaver, laser, or ultrasonic scalpel. In certain embodiments, the surgical instrument holder is for use in spinal surgery. In certain embodiments, the surgical instrument is a screw driver (e.g., for placing a screw in a hole).

In certain embodiments, a user interface (e.g., touch screen, one or more buttons, and/or a display). In certain embodiments, the tubular structure has an interior surface sized and shaped to accommodate a tool support (e.g., sliding surface) of the surgical instrument. In certain embodiments, a second connector associated with the surgical instrument holder that communicates with a sensor (e.g., the force sensor(s)) measuring the position of the surgical instrument. In certain embodiments, the second connector is one or more brushes (e.g., that physically contact the surgical instrument). In certain embodiments, the rigid hollow tubular structure is a cylindrical structure.

The disclosed technology, in certain embodiments, includes a robotic surgical system for performing surgery. In certain embodiments, a robotic arm with an end effector comprising a surgical instrument holder sized and shaped to hold and/or restrict movement of a surgical instrument therethrough, the surgical instrument holder comprising: a rigid hollow tubular structure having a proximal open end and a distal open end, said structure defining an axis along which movement of a surgical instrument (e.g., fitted with a tool support) sliding through the structure is restricted, wherein the tubular structure has an interior surface shaped and sized to accommodate the surgical instrument sliding through the surgical instrument holder such that movement of the tool support is constrained to move along the axis defined by the surgical instrument holder, wherein the tubular structure has an exterior surface comprising at least one flange that is sized and shaped to securely couple of the surgical instrument holder to an end effector of the robotic surgical system, and wherein the tubular structure comprises a longitudinal notch along its length, wherein the longitudinal notch is sized in relation to a peg on the tool support to permit the tool support to slide along the axis defined by the surgical instrument holder; a lock that, when engaged, restricts (e.g., prevents) movement of a surgical instrument within the rigid hollow tubular structure (e.g., such that the surgical instrument is constrained within the tubular structure in all directions); and a connector element associated with (e.g., attached to) the surgical instrument holder that, when engaged with (e.g., mated with) a corresponding connector associated with the surgical instrument connector, provides power to the surgical instrument (e.g., and information transfer, e.g., information concerning measured forces).

The disclosed technology, in certain embodiments, includes a manipulator that allows robotically-assisted or unassisted positioning and/or movement of the surgical instrument holder by a user with at least four degrees of freedom to align an axis defined by the instrument holder at a desired trajectory in relation to a patient situation.

The disclosed technology, in certain embodiments, includes a surgical instrument holder for use with a robotic surgical system. In certain embodiments, the surgical instrument holder includes a rigid hollow tubular structure having a proximal open end and a distal open end, said structure defining an axis along which movement of a surgical instrument (e.g., fitted with a tool support) sliding through the structure is restricted, wherein the tubular structure has an interior surface shaped and sized to accommodate the surgical instrument sliding through the surgical instrument holder such that movement of the tool support is constrained to move along the axis defined by the surgical instrument holder, wherein the tubular structure has an exterior surface comprising at least one flange that is sized and shaped to securely couple the surgical instrument holder to an end effector of the robotic surgical system, and wherein the tubular structure comprises a longitudinal notch along its length, wherein the longitudinal notch is sized in relation to a peg on the tool support to permit the tool support to slide along the axis defined by the surgical instrument holder; and a lock that, when engaged, restricts (e.g., prevents) movement of a surgical instrument within the rigid hollow tubular structure (e.g., such that the surgical instrument is constrained within the tubular structure in all directions); a connector element associated with (e.g., attached to) the surgical instrument holder that, when engaged with (e.g., mated with) a corresponding connected associated with the surgical instrument, provides power to the surgical instrument (e.g., and information transfer, e.g., information concerning measured forces).

In certain embodiments, a force sensor for measuring one or more forces and/or torques (e.g., 1 to 3 forces and 1 to 3 torques) applied to at least a portion of the surgical instrument. In certain embodiments, the surgical instrument comprises a force sensor for measuring one or more forces and/or torques (e.g., 1 to 3 forces and 1 to 3 torques) applied to at least a portion of the surgical instrument.

The disclosed technology, in certain embodiments, includes a surgical instrument for preparing a hole in bone tissue of a patient.

In certain embodiments, the surgical instrument includes an elongate structure having a proximal end with at least one of a drilling, milling, or shaving surface and a distal end with a shank sized and shaped to be grasped by a drill; and a force sensor integrated directly in the elongate structure for measuring one or more forces and/or torques (e.g., 1 to 3 forces and 1 to 3 torques) applied to at least a portion of the surgical instrument.

In certain embodiments, the surgical instrument includes an elongate structure having a proximal end with a milling surface and a distal end with a shank sized and shaped to be grasped by a drill, wherein the proximal end of the surgical instrument is flat and substantially perpendicular to the axis of the elongate structure, thereby reducing skidding (e.g., unintentional lateral movement of the surgical instrument) of the surgical instrument upon contact of the milling surface with the bone tissue; and a force sensor integrated directly in the elongate structure for measuring one or more forces and/or torques (e.g., 1 to 3 forces and 1 to 3 torques) applied to at least a portion of the surgical instrument.

In certain embodiments, a portion of the structure of the surgical instrument closest to the milling surface is for milling (e.g., rather than drilling) and the remaining portion of the surgical instrument is for drilling. In certain embodiments, the surgical instrument is an anti-skip surgical instrument. In certain embodiments, the surgical instrument is for use in spinal surgery. In certain embodiments, the surgical instrument is insertable into a surgical instrument holder such that the surgical instrument is constrained by the surgical instrument holder. In certain embodiments, the surgical instrument holder comprises a rigid hollow tubular structure having a proximal open end and a distal open end, said structure defining an axis of the tubular structure along which movement of a surgical instrument sliding through the structure is restricted, wherein the tubular structure has an interior surface shaped and sized to accommodate the surgical instrument sliding through the surgical instrument holder such that movement of the surgical instrument (e.g., fitted with a tool support) is constrained to move along the axis defined by the surgical instrument holder.

In certain embodiments, the surgical instrument is fitted with a tool support shaped and sized to slide through the surgical instrument holder along the axis defined by the surgical instrument holder. In certain embodiments, the surgical instrument is a drill bit and the surgical instrument holder is a drill bit guide holder. In certain embodiments, the surgical instrument is held by a robotic surgical system comprising a robotic arm.

In certain embodiments, the robotic arm has an end effector comprising a surgical instrument holder attached thereto, the surgical instrument holder sized and shaped to hold and/or restrict movement of a surgical instrument therethrough (e.g., via a lock). In certain embodiments, a navigation marker is used by a navigation camera to track the surgical instrument.

The disclosed technology, in certain embodiments, includes a method of performing surgery with a robotic surgical system. The method, in certain embodiments, includes moving a mobile cart transporting a robotic surgical system comprising a robotic arm in proximity to an operating table, wherein the robotic arm has an end effector comprising a surgical instrument guide attached thereto, the surgical instrument guide sized and shaped to hold and/or restrict movement of one of a plurality of surgical instruments therethrough, wherein the plurality of surgical instruments comprises a first surgical instrument (e.g., for removing tissue from the body) and a second surgical instrument (e.g., for preparing a screw placement in a vertebra); stabilizing the mobile cart; maneuvering the first surgical instrument in a manner that is constrained by a surgical instrument guide comprising a rigid hollow tubular structure having a proximal open end and a distal open end, said structure defining the axis along which movement of a surgical instrument (e.g., fitted with a tool support) sliding through the structure is restricted, wherein: the tubular structure of the surgical instrument guide has an interior surface shaped and sized to accommodate the surgical instrument sliding through the guide such that movement of the surgical instrument is constrained to move along the axis defined by the guide, and the tubular structure comprises a longitudinal notch along its length, wherein the longitudinal notch is sized in relation to a peg to (i) permit a marker attached to the surgical instrument at least in part via the peg to be viewable by a navigation camera along an entire range of movement of the surgical instrument through the guide, (ii) constrain movement of the navigation marker in a fixed orientation along the axis defined by the guide, and/or (iii) permit the surgical instrument to slide along the axis defined by the guide while the guide is held in a fixed position by the robotic surgical system; removing the first surgical instrument from the surgical instrument guide, wherein the surgical instrument guide facilitates rapid exchange of surgical instruments (e.g., without requiring reregistration); and maneuvering the second surgical instrument in a manner that is constrained by a surgical instrument guide.

In certain embodiments, the first surgical instrument is a drill (e.g., with a drill bit). In certain embodiments, the first surgical instrument is a milling device, shaver, laser, and ultrasonic scalpel.

In certain embodiments, the second surgical instrument is a screw driver (e.g., for placing a screw in a hole). In certain embodiments, the second surgical instrument is a drill (e.g., for preparing a hole for receiving a screw). In certain embodiments, the tubular structure has an exterior surface comprising at least one flange that is sized and shaped to securely couple the surgical instrument holder to an end effector of the robotic surgical system. In certain embodiments, the robotic surgical system is for use in spinal surgery. In certain embodiments, the rigid hollow tubular structure is a cylindrical structure. In certain embodiments, the longitudinal notch is a slot. In certain embodiments, the navigation marker is used by a navigation camera to track the surgical instrument. In certain embodiments, the second surgical instrument is used to guide a screw implant and a tissue protector. In certain embodiments, the robotic arm comprises a manipulator attached to the robotic arm. In certain embodiments, the robotic arm comprises a manipulator molded into the robotic arm.

In certain embodiments, stabilizing the mobile cart comprises extracting one or more rigid legs on the mobile cart such that the mobile cart rests on the one or more rigid legs of the mobile cart. In certain embodiments, stabilizing the mobile cart comprises retracting one or more wheels on the mobile cart such that the mobile cart rests on one or more rigid legs of the mobile cart.

The disclosed technology, in certain embodiments, includes a method of performing surgery with a robotic surgical system. In certain embodiments, the method includes identifying a volume to be removed, wherein medical images (e.g., obtained intra-operatively or pre-operatively) of the patient situation displayed on a display (e.g., on the robotic surgical system) are automatically updated to show feedback about the planning (e.g., displaying the volume identified for removal by shading); removing the planned volume using robotic assistance, the removing comprising: storing, by a processor of the robotic surgical system, a location of the volume to be removed as "stay-in zone", and storing, by the processor, a location of a second volume to protect from removal, wherein the location of the second volume defines a "no-go zone"; maintaining, by the processor, the surgical instrument in the "stay-in zone" and/or out of the "no-go zone", thereby removing the volume; after removing at least a portion of the volume, moving at least a portion of the robotic surgical system away from the patient; and manually completing the surgery.

The disclosed technology, in certain embodiments, includes a method of performing surgery with a robotic surgical system. The method, in certain embodiments, includes identifying a volume to be removed, wherein medical images (e.g., obtained intra-operatively or pre-operatively) of the patient situation displayed on a display (e.g., on the robotic surgical system) are automatically updated to show feedback about the planning (e.g., displaying the volume identified for removal by shading); removing the planned volume using robotic assistance, the removing comprising: preventing, by the robotic surgical system, a surgical instrument from leaving the volume until the volume is completely removed or the surgeon voluntarily wants to leave the volume; after removing at least a portion of the volume, moving at least a portion of the robotic surgical system away from the patient; and manually completing the surgery.

In certain embodiments, the volume is identified by identifying (e.g., using a navigation system) a plurality of points on the patient anatomy. In certain embodiments, the plurality of points are identified by a surgeon point to a plurality of points on the patient anatomy (e.g., using a pointer tracked by a navigation system). In certain embodiments, the plurality of points are identified by following a path identified by a surgeon (e.g., via a pointer tracked by a navigation system) such that the plurality of points are automatically collected. The volume can be identified using a navigation system. Additionally, the volume can be identified using automatic segmentation, semi-automatic segmentation (e.g., using surgeon-defined points or corrections), or fully manual when surgeon/assistant/neurologist defines volume by manually selecting etc. the "pixels"/"voxels" to be removed.

In certain embodiments, the method includes manually completing the surgery includes removing, by the surgeon, a portion of the volume to be removed. In certain embodiments, manually completing the surgery includes removing, by the surgeon, a portion of a second volume adjacent the volume removed with assistance of the robotic surgical system.

In certain embodiments, repulsive/wall-like forces prevent the surgeon from moving a position of the surgical instrument into the second volume.

In certain embodiments, the method includes triggering a dead-man switch (e.g., via voice recognition, a gesture, presence or absence of physical contact with a portion of the robotic surgical system), thereby causing the robotic surgical system to stop.

In certain embodiments, the method includes, upon receiving a trigger signal (e.g., from a volume removal force sensor, a bio-sensing device such as PediGuard® by SpineGuard S.A. of Vincennes, France, and/or a neuro-monitoring device), preventing movement of the surgical instrument further in a forbidden direction.

In certain embodiments, the method includes, after identifying the volume to be removed, bringing the robot to the volume (e.g., automatically or using hands-on control). In certain embodiments, the identification of the volume is performed using a navigation system pointer. In certain embodiments, the identification of the volume is performed using the robotic surgical system in a force control mode.

In certain embodiments, the method includes maneuvering a surgical instrument to make an incision, thereby exposing a vertebra; and attaching a frame of a navigation system to the patient.

In certain embodiments, the method includes moving a mobile cart transporting a robotic surgical system comprising a robotic arm in proximity to an operating table, wherein the robotic arm has an end effector comprising a surgical instrument holder attached thereto, the surgical instrument holder sized and shaped to hold and/or restrict movement of a surgical instrument therethrough; and stabilizing the mobile cart.

In certain embodiments, the method includes removing a least a portion of the spinous process, discs, facets, facet joints, pedicles, and/or vertebral bodies. In certain embodiments, the method includes a first force sensor and a second force sensor, each of the first and second force sensors for measuring one or more forces and/or torques (e.g., 1 to 3 forces and 1 to 3 torques) applied to at least a portion of the surgical instrument.

In certain embodiments, the surgical instrument holder, surgical instrument, and/or robotic surgical system is for use in at least one of spinal surgery (e.g. laminotomy), neurosurgery (various types of craniotomy), ENT surgery (e.g. tumor removal), and orthopedic surgery (bone removal).

In another aspect, the disclosed technology includes a tool attachment device for attaching a tool to a robotic surgical arm, the tool attachment device including: a lever for transmitting a fixation force to a quick lock latch via a plurality of links; and the quick lock latch for releasably securing a tool to the robot when an activation force is applied to the lever (e.g., the lever pulling the tool tight against a robot flange).

In certain embodiments, the lever is activated by pushing the lever toward a robot flange such that quick lock latch pulls the tool tight against the robot flange.

In certain embodiments, the quick lock latch comprises a quick lock hook that engages a pin head on the tool when the tool is inserted fully into the robot flange.

In certain embodiments, a positioning module for precisely positioning the surgical instrument holder relative to the robotic surgical arm (e.g., restricting orientation of the tool when mounting the tool to the robot).

In certain embodiments, the positioning module comprises one or more pins on the robot flange, wherein, upon mechanically coupling the tool to the robotic surgical arm, the each pin of the one or more pins engage an opening in the tool thereby precisely positioning the tool relative to the robotic surgical arm.

In certain embodiments, the positioning module comprises one or more openings on the robot flange, wherein, upon mechanically coupling the tool to the robotic surgical arm, the each opening of the one or more opening engages a pin on the tool thereby precisely positioning the tool relative to the robotic surgical arm.

In another aspect, the disclosed technology includes a tool attachment device for attaching a tool to a robotic surgical arm, the tool attachment device including: a robot flange on the robotic surgical arm, the robot flange comprising (i) an open portion to receive a protrusion of a tool and (ii) a notch that permits a width of the opening to be at least partially decreased; and a lever connected to the robot flange that causes the width of the open portion of the robot flange to decrease when the lever is engaged, thereby securing the tool with the protrusion positioned in the opening to the robot flange.

In another aspect, the disclosed technology includes a tool attachment device for attaching a tool to a robotic surgical arm, the tool attachment device including: a robot flange on the robotic surgical arm, the robot flange comprising a shape lock (e.g., bayonet mount) having at least two or more openings each arranged to receive and secure a protrusion on the tool or at least two or more protrusions each arranged to engage and secure an opening on the tool.

In another aspect, the disclosed technology includes a drill for use with a surgical robotic arm, the drill including: a chuck for securely holding a drill bit; and a body comprising a positioning module for precisely positioning the drill relative to the robotic surgical arm.

In certain embodiments, the body of the drill comprises a protrusion and the protrusion comprises a pin head.

In certain embodiments, the positioning module comprises one or more pins on the body, wherein, upon mechanically coupling the drill to the robotic surgical arm, each pin of the one or more pins engages an opening in the surgical robotic arm thereby precisely positioning the drill relative to the robotic surgical arm.

In certain embodiments, the positioning module comprises one or more openings on the body, wherein, upon mechanically coupling the drill to the robotic surgical arm, the each opening of the one or more opening engages a pin on the robot thereby precisely positioning the drill relative to the robotic surgical arm.

In certain embodiments, the positioning module comprising a hole that passes from a first side of the body to a second side of the body (e.g., such that the body can be mounted on the robot (e.g., by a bolt extending from the robotic surgical arm that slides through the hole and a nut that securely holds the body on the robotic surgical arm)).

In certain embodiments, the positioning module is a friction based module and comprises a protrusion that fits into a portion of the robot flange and is secured therein by a force applied by a lever attached to the robot flange.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 11A through 11F illustrate an example system for securing an instrument to a robot in accordance with an embodiment of the invention;

Figure 1:
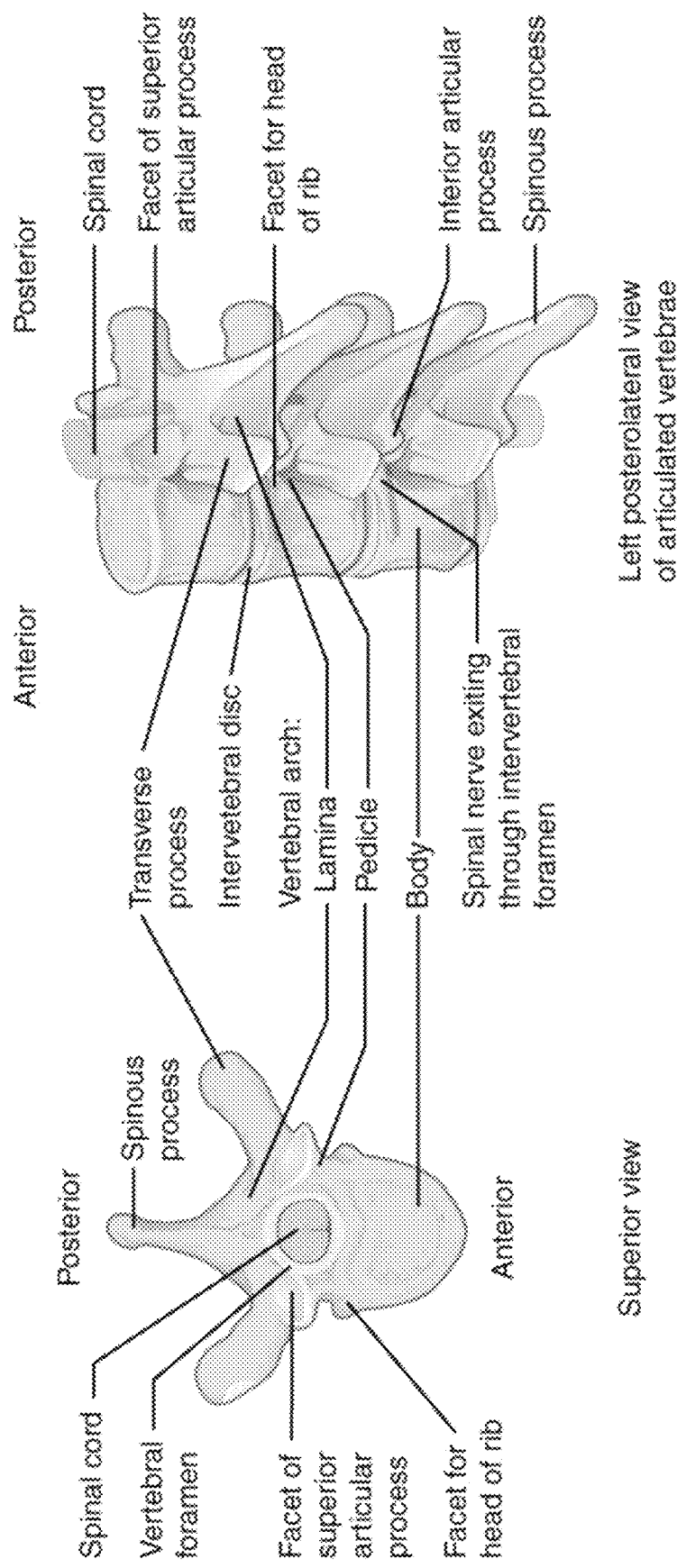
FIG. 1 is a superior view and left posterolateral view of articulated vertebrae.
Figure 2B:
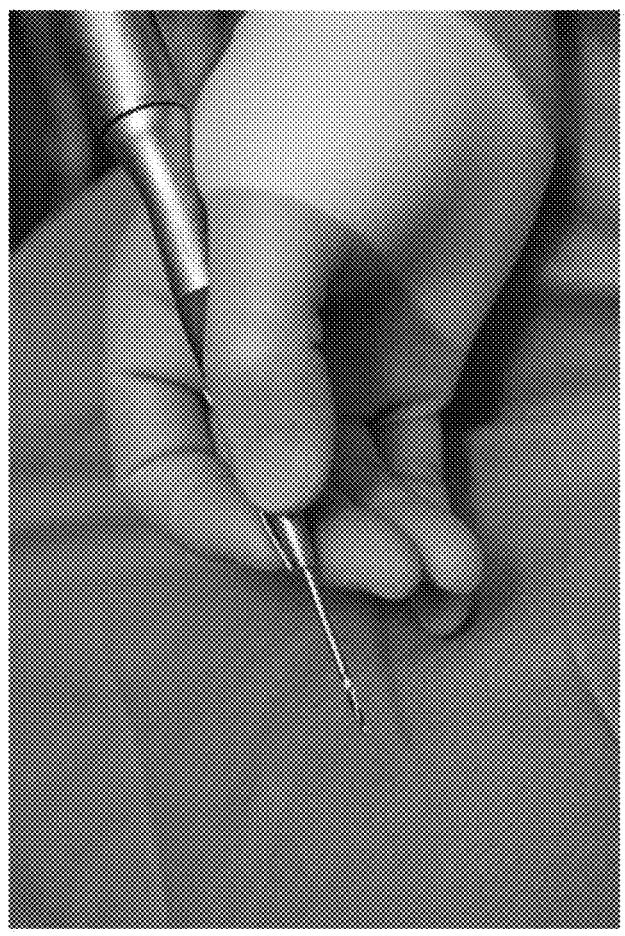
FIGS. 2A and 2B are illustrations of surgical pliers and a high-speed burr, respectively.
Figure 2A:
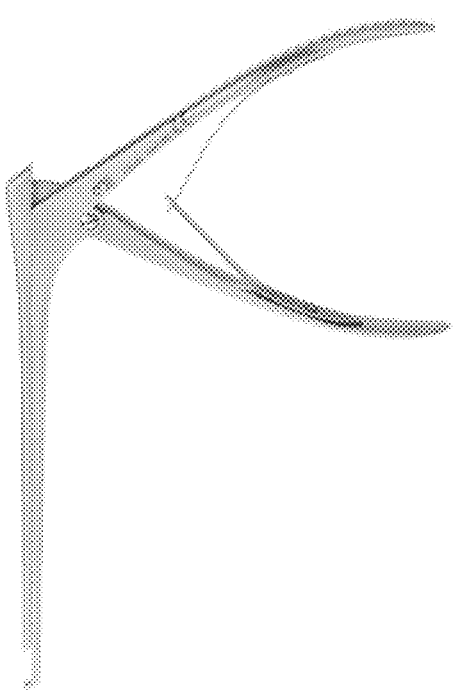

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

The disclosed technology includes the robotic surgical system used to remove a target volume from a patient. Initially, an incision is made and the vertebra is exposed. In some implementations, the frame of a navigation system is attached to the patient in the place selected by the surgeon. Intra-operative medical images of the target anatomy may be obtained. Alternatively, images are acquired pre-operatively. Once the images are obtained, the images must be matched to the actual patient position by a process called registration. For intra-operative images, an automatic algorithm may be used to register the actual patient position with the intra-operative images. Alternatively, point-to-point registration or surface matching may be used. The disclosed technology provides an effective and quick way for the surgeon to define volume to be removed and thereafter remove the volume. In another example, the robotic surgical system may be used to place a screw in a vertebra by assisting in drilling a hole and inserting the screw in the hole as described in U.S. patent application Ser. No. 14/266,769, filed Apr. 30, 2014, and entitled "Apparatus, Systems, and Methods for Precise Guidance of Surgical Tool" which is hereby incorporated by reference in its entirety.

Figure 3:
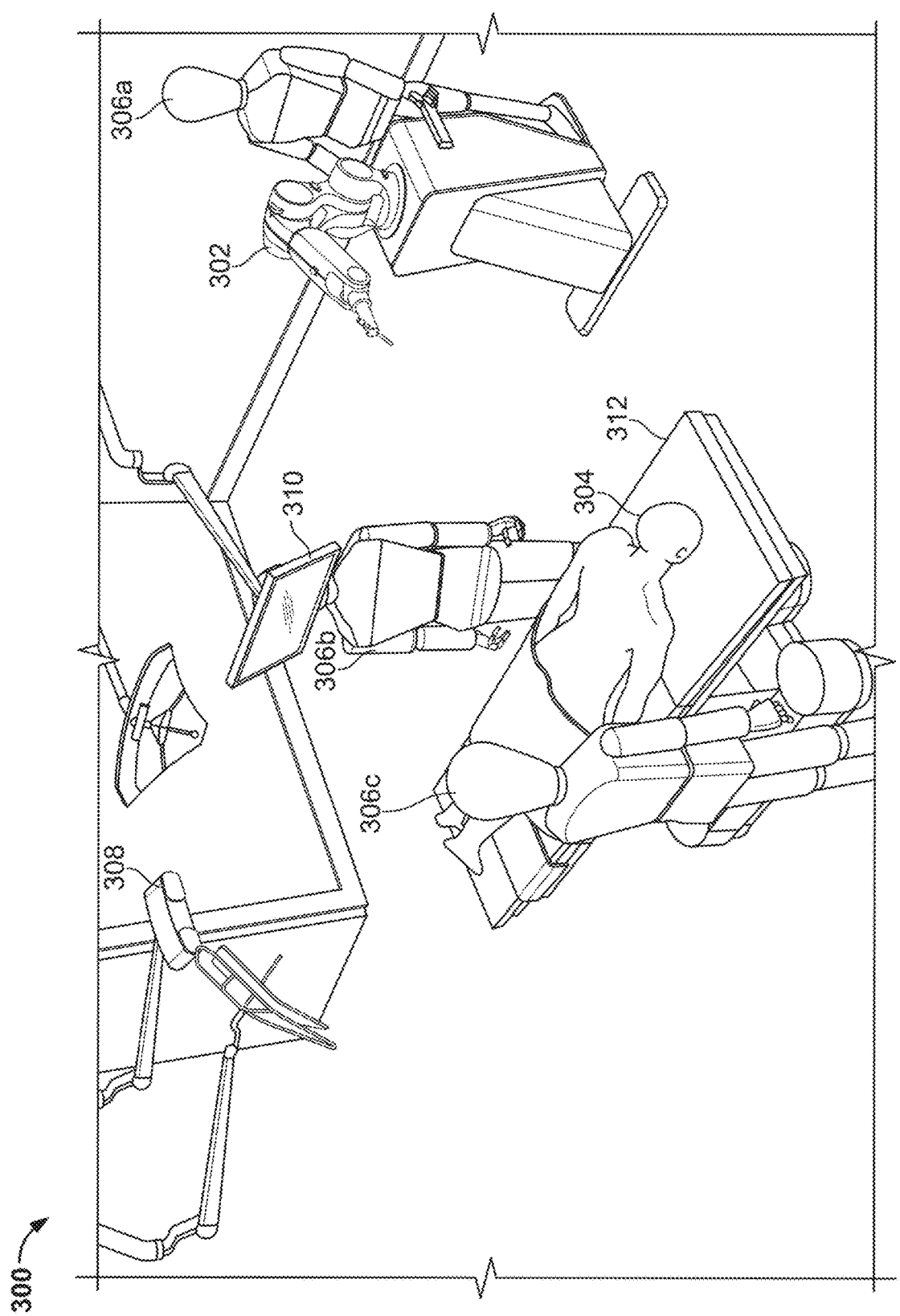
FIG. 3 is an illustration of an example robotic surgical system in an operating room.

FIG. 3 illustrates an example robotic surgical system in an operating room 300. In some implementations, one or more surgeons, surgical assistants, surgical technologists and/or other technicians, (306a-c) perform an operation on a patient 304 using a robotic-assisted surgical system. In the operating room the surgeon may be assisted by the robotic system to accurately execute an operation.

In some implementations, the surgical robotic system includes a surgical robot 302 on a mobile cart. The surgical robot 302 may be positioned in proximity to an operating table 312 without being attached to the operating table itself, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 306a, such as a technician, nurse, surgeon, or any other medical personnel in the operating room, to move the surgical robot 302 to different locations before, during, and/or after a surgical procedure. The mobile cart enables the surgical robot 302 to be easily transported into and out of the operating room 300. For example, a user 306a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization mechanism increases the global stiffness of the mobile cart relative to the floor in order to ensure the accuracy of the surgical procedure. In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 302 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the surgical system includes a tracking detector 308 that captures the position of the patient and different components of the surgical robot 302, and a display screen 310 that displays, for example, real time patient data and/or real time surgical robot trajectories.

For example, a tracking detector 308 monitors the location of patient 304 and the surgical robot 302. The tracking detector may be a camera, a video camera, an infrared detector, field generator and sensors for electro-magnetic tracking or any other motion detecting apparatus. In some implementation, based on the patient and robot position, the display screen displays the target volume to be removed and/or the volume already removed. These different volumes may be differentiated on the display using various colors or shading. By continuously monitoring the patient and robotic arm positions using tracking detector 308, the surgical system can visually display the target and/or removed volume on display screen 310 to inform and guide surgeons and/or technicians in the operating room using the surgical robot. For instance, the location of the end-effector can be automatically adjusted in real time to account for movement of the vertebrae or other part of the patient during the surgical procedure.

Figure 4:
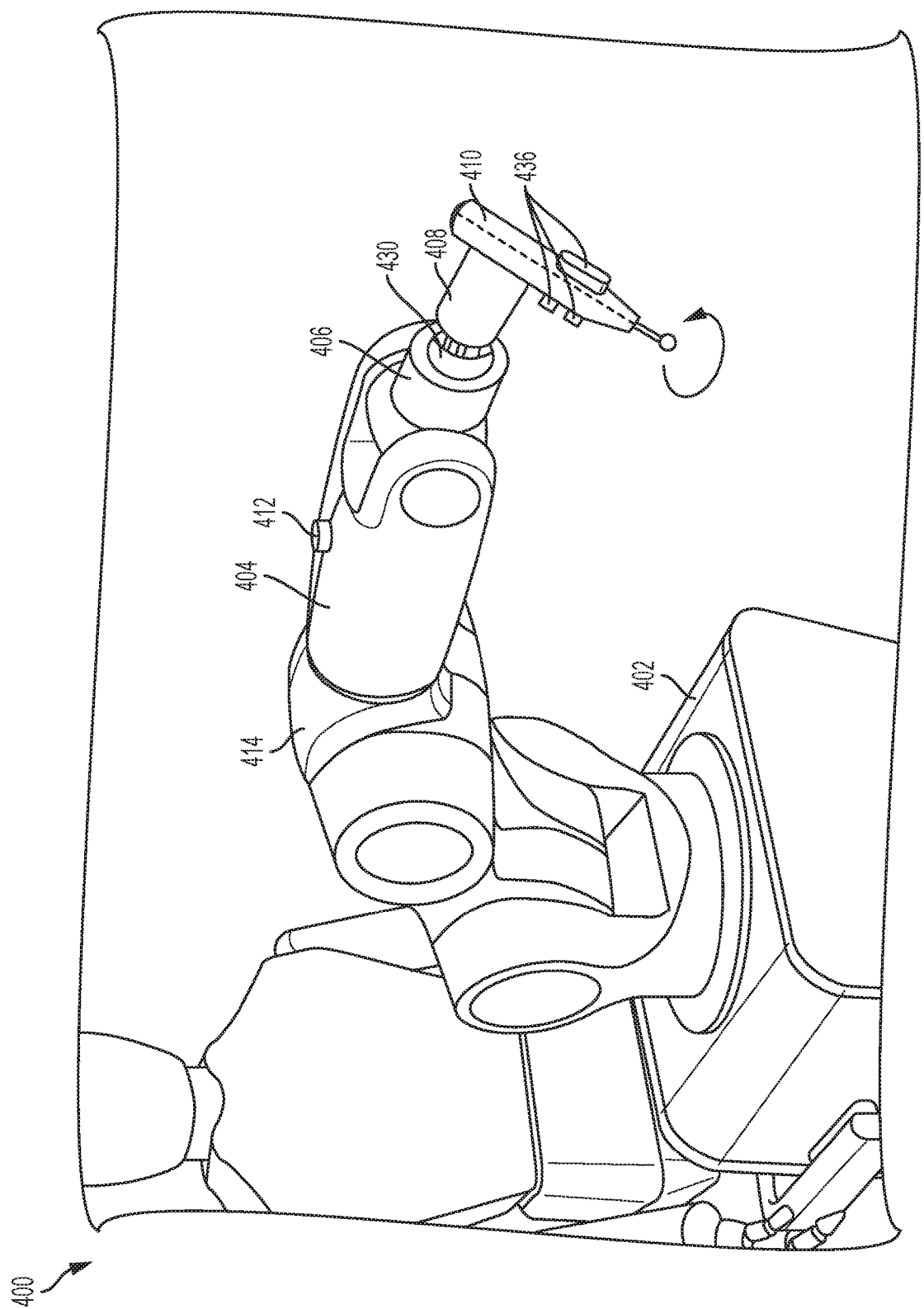
FIG. 4 is an illustration of an example robotic surgical system.

FIG. 4 illustrates an example configuration 400 of a robotic arm for performing a surgical operation involving the removal of a volume from a patient. A surgical tool holder 408, in some implementations, is connected (e.g., removably; e.g., directly or indirectly) to the robot arm 404. For example, the surgical tool holder 408 is removably connected to the robotic arm 404 via connector 406 and a force sensor 430 as shown in FIG. 4. In some implementations, the robot arm 414 is extended so that a tool holder 408 may be placed on the robot arm connector 406. In some embodiments, a robot arm connector 406 is located at the end of the robot manipulator 404. Although not shown in FIG. 4, a surgical drape may be placed over the robot arm 414 and cart 402 when the tool holder 408 is inserted into, or otherwise attached to, the connector 406. The connector 406 may be configured to at least partially protrude from the surgical drape, such that a sterile cap, collar, or other covering of the connector may be installed prior to attachment of the tool holder 408 into the connector 406 to maintain sterile seal.

The robot arm connector 406 is configured to pass electrical signals from the rest of robot arm 414 to the tool holder 408. The electrical signals may be passed by a separate cable that passes through the sterile drape. The cable may be integrated with the sterile drape to simplify handling for the user. An operator attaches the tool holder 408 to the robot arm connector 406. In the embodiment shown in FIG. 4, the tool holder 408 is a drill holder for securely holding a drill.

The tool holder 408, in some implementations, is a surgical tool holder that may be used to hold various surgical tools and/or allow insertion of one or more surgical tools/implements therethrough. The surgical tool 410, in some implementations, provides an accurate tool guide for surgical bone drilling, e.g., by providing a precisely aligned shaft through which a drill bit or drill may be inserted. Surgical tool 410 is used in spinal surgeries to allow for accurate surgical instrument placement. In some implementations, the surgical tool 410 is a drill that is directly connected to the tool holder 408, thereby securely holding a drill for removing a volume from a patient. The surgical tool may be any instrument which can be used for removing tissues. For example, the surgical tool 410 may be a drill, mill, shaver, laser, or ultrasonic scalpels. In some implementations, the tool holder 408 may be used both to securely hold a tool for removing a volume from a patient and placing a screw in a vertebra.

A force sensor 430, in some implementations, is placed between the robot arm connector 406 and the tool holder 408. The force sensor 430 measures forces applied to a surgical instrument 410 held by the tool holder 408. The force sensor 430 may be placed in a variety of locations. In some implementations, multiple force sensors 430 are used. For example, multiple force sensors 430 may be used to provide redundant measurements for safety reasons. Additionally, multiple force sensors 430 may be used to extract additional force information (e.g., determining where the forces are applied). In some implementations, the robot arm manipulator 404 includes an emergency stop switch 412. The emergency stop switch may be placed on the robot arm, robot cart, or on the operator's panel. A user interface 436, in some implementations, is integrated into the surgical instrument 410 to allow a user quick and easy interaction with the system. Several placements of user interfaces can be used. For direct and immediate interaction a sterile user interface is placed on the surgical instrument or tool holder. In other implementations, the interface can be placed on the robot arm as described in U.S. patent application Ser. No. 14/858,325, filed Sep. 18, 2015, and entitled "Robot-Mounted User Interface For Interacting with Operation Room Equipment" which is hereby incorporated by reference in its entirety. In some implementations, user interfaces are provided in multiple locations, such as on the robot arm, the surgical instrument, tool holder, and/or manipulator (e.g., handle) as described in U.S. patent application Ser. No. 14/619,732, filed Feb. 11, 2015, and entitled "Sterile Handle for Controlling a Robotic Surgical System from a Sterile Field" a which is hereby incorporated by reference in its entirety. The sterile interfaces can be reusable or disposable.

Figure 5C:
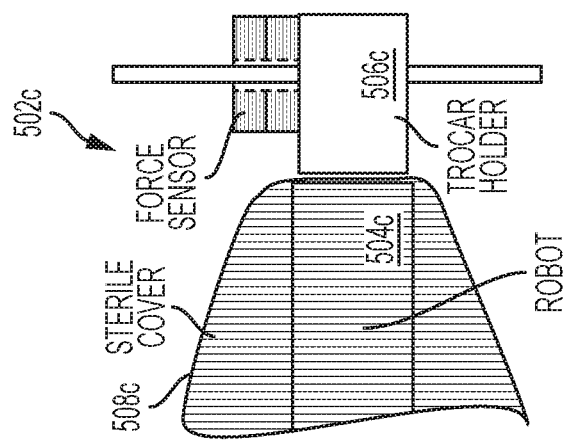
FIGS. 5A through 5C are illustrations of an example force sensor implementations.
Figure 5B:
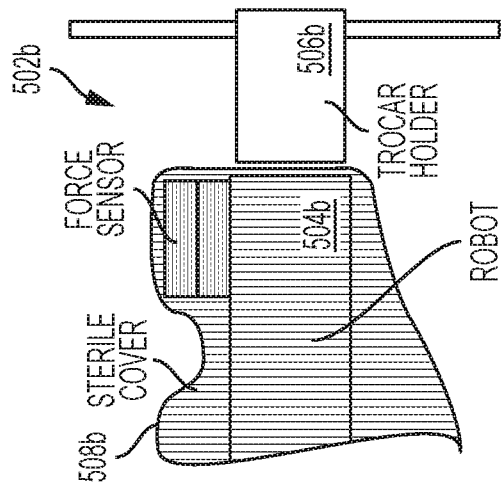
Figure 5A:
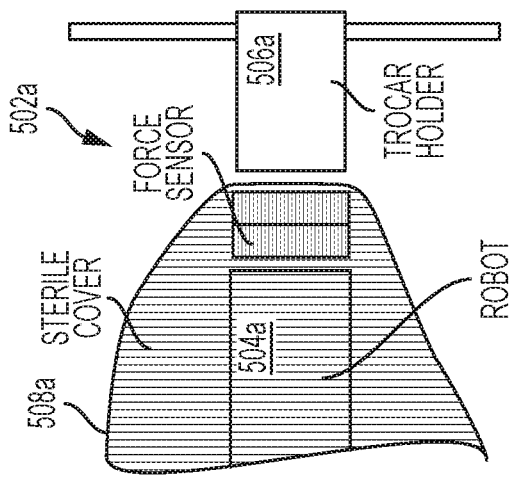

FIGS. 5A-C illustrate example locations for mounting a force sensor (e.g., force/torque sensor 430). In some implementations, as shown in FIG. 5A, the force sensor 502a is located between the tool holder 506a and robot 504a. Using this configuration, the sterile cover 508a may be wrapped around the robot arm and between the force sensor and the tool holder to ensure sterilization. The force sensor 502a may provide for direct measurement of forces (e.g., forces and/or torques) on the tool. The force sensor 502a may be designed to resist flexing. The force sensor 502a may be designed to flex under the stress of certain external forces. The displacement caused when an external force is applied may be calculated based on the force and/or torque applied to the tool, radial force stiffness, axial torque stiffness, and the diameter of the holder to which the tool is attached.

As shown in FIGS. 5B and 5C, respectively, the force sensor (e.g., 502b in FIG. 5B or 502c in FIG. 5C) may be located on the robot or the tool holder, respectively. These configurations may exclusively measure the forces and/or torques applied by the user. The force sensor 508 may be connected to the robot with an intermediary analog box which measures forces and torques and transmits them via a network (e.g., Ethernet, CAN, wireless, internet, private LAN, public LAN, etc.). Combinations of the above mentioned force sensor positions are possible to achieve predefined behavior (e.g. the first sensor in the base FIG. 5A and the second one in the handle FIG. 5B may be positioned to allow the feedback control system to decouple forces applied to the surgical tool from forces and/or torque applied by a user).

Figure 6:
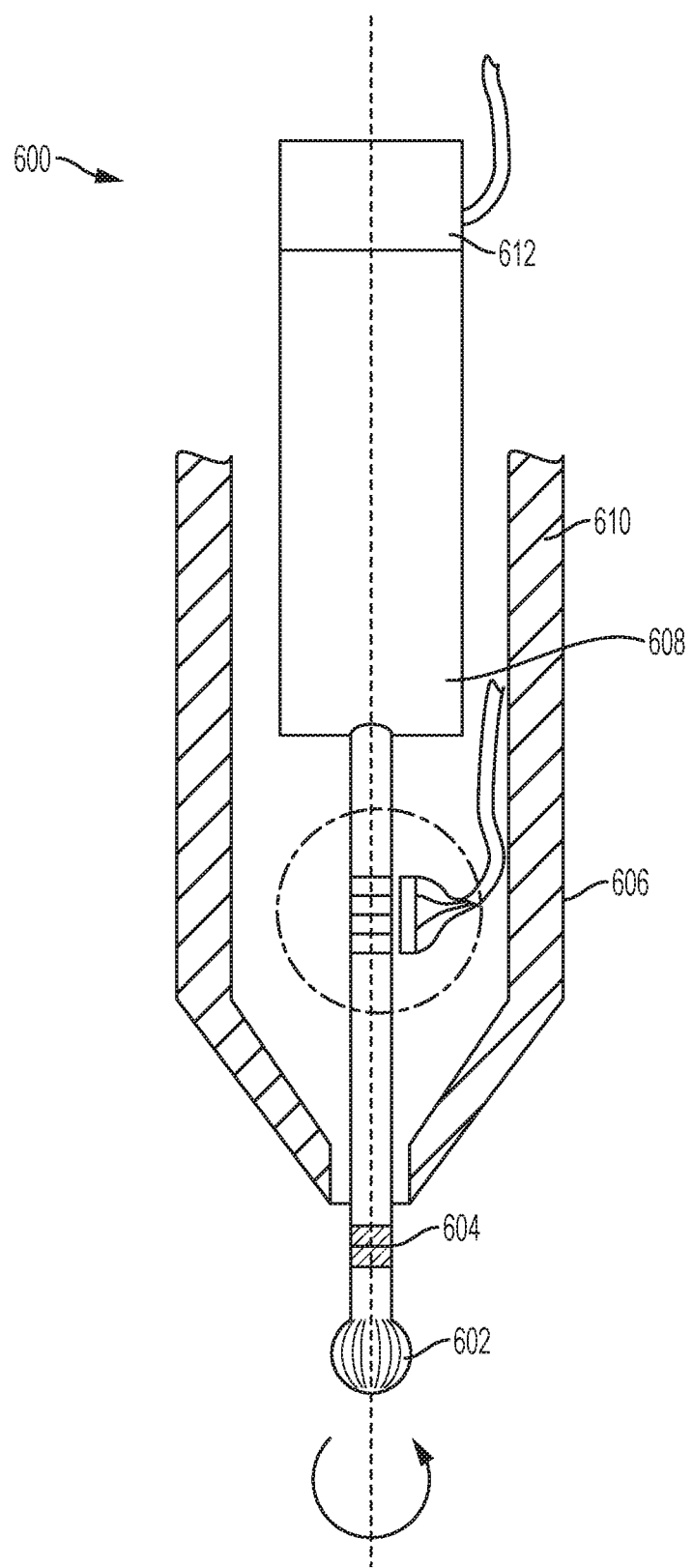
FIG. 6 is an illustration of an example surgical instrument.

Additionally, in some implementations the force sensor is integrated directly in the surgical instrument. For example, the force sensor may be integrated directly in the surgical drill bit as illustrated in FIG. 6. While the implementation of the force sensor 604 is described in relation to a drill bit 602 as shown in FIG. 6, the force sensor 604 may be similarly integrated in other surgical instruments. Integrating the force sensor 604 in a surgical instrument, such as a drill bit 602, may be more robust as it minimizes the impact of external disturbances for measuring forces applied to the drill bit.

In the example configuration shown in FIG. 6, the force sensor 604 is integrated in the shaft of the drill bit 602. The force sensor 604, in some implementations, is located on the drill bit 602 outside of the body 610 of the drill as shown in FIG. 6. In other implementations, the force sensor 604 is located inside the body 610 of the drill, thereby better protecting the force sensor 604 from external influences. Force sensor can have multiple degrees of freedom and measure, for example, 1 to 3 forces and/or 1 to 3 torques. Forces are transmitted from the rotating shaft through a connector 606. The connector, in some implementations, is one or more brushes that provide an electrical connection to the force sensor 604. If the force sensor is an optical sensor, the connector may be an optical transmitter (e.g. LED) and/or optical receiver (e.g., photodiode). In this example, the brushes contact the drill bit thereby forming an electrical connection with the force sensor 604. In some implementations, the brushes touch one or more contacts on the drill bit to form the electrical connection.

An electric or pneumatic motor 608 rotates the drill bit 602 shaft. In some implementations, a sensor 612 (e.g., an encoder) measures position of the shaft. The sensor 612 measures the position of the shaft in order to correlate forces measured by the force sensor to the relative position of the shaft. For example, if the force sensor is located in a drill bit, the measurement of the direction of the force will vary as the drill bit rotates. Specifically, the force sensor measures force and the direction of the force periodically (e.g., every millisecond, every microsecond, or somewhere therebetween). The drill bit rotates as the surgeon pushes it into bone. When the drill contacts the bone, the force sensor will indicate some force (F1) in a direction (D1). One period later (e.g., one millisecond), the drill bit will rotate slightly so the force sensor will indicate force of the same value (F1) (assuming a constant force is applied) in a different direction (D2). The direction of the force will continue to change relative to a single perspective as the drill bit rotates even if surgeon pushes into the bone with a constant force. A constantly changing force direction is not acceptable. In order to correlate the directions (e.g., D1, D2) with the global direction of the force (D) coming from the bone (seen by the surgeon, robotic system etc.) the position of the drill in the global space must be calculated as the drill bit rotates. The sensor 612 is used to measure the position of the shaft and thus determine the global direction of the force (D). The sensor 612 may be located on the back of the motor 608 as shown in FIG. 6. The sensor 612 may be located in other locations relative to the motor 608 as well.

The force sensor 604 may be provided in various configurations as shown in FIGS. 7A-D. In each configuration, the goal is to measure forces on the tip of the tool (e.g., drill bit ultrasound bit, etc.). In the example shown in FIG. 7A the force sensor 604 is integrated in the shaft of the drill bit 602 as described in relation to FIG. 6. The force sensor 604 may communicate with a connector 606 (shown in FIG. 6) via a sensor cable 702. The sensor cable 702, in some implementations, is routed inside the drill bit 602. In some implementations, the connector 606 (shown in FIG. 6) is electrically connected to the sensor cable 702 via one or more connection pads.

Figure 7A:
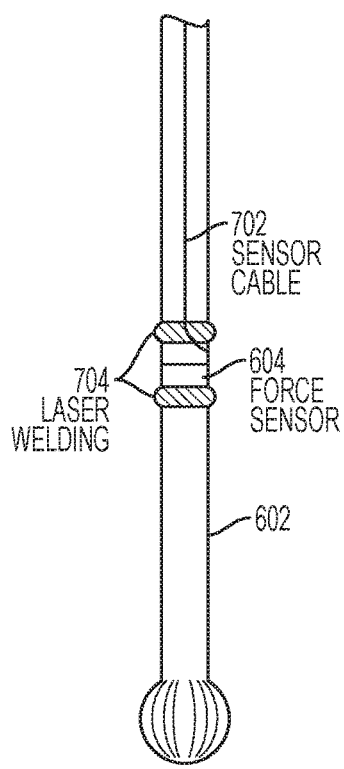
FIGS. 7A through 7D are illustrations of an example implementations of a force sensor integrated in a surgical drill.
Figure 7B:
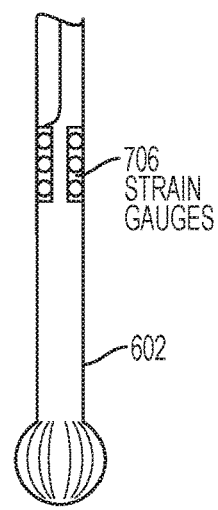

The force sensor 604 in this example may be a miniaturized industrial sensor (e.g., the multi-axis force/torque sensor from ATI Industrial Automation, Inc. of Apex, N.C.) that measures, for example, all six components of force and torque using a transducer. Alternatively, the force sensor 604 may be an optical sensor. Alternatively, the force sensor 604 may comprise a strain gauge 706 integrated directly into the shaft of the drill bit 602 as shown in FIG. 7B.

Figure 7C:
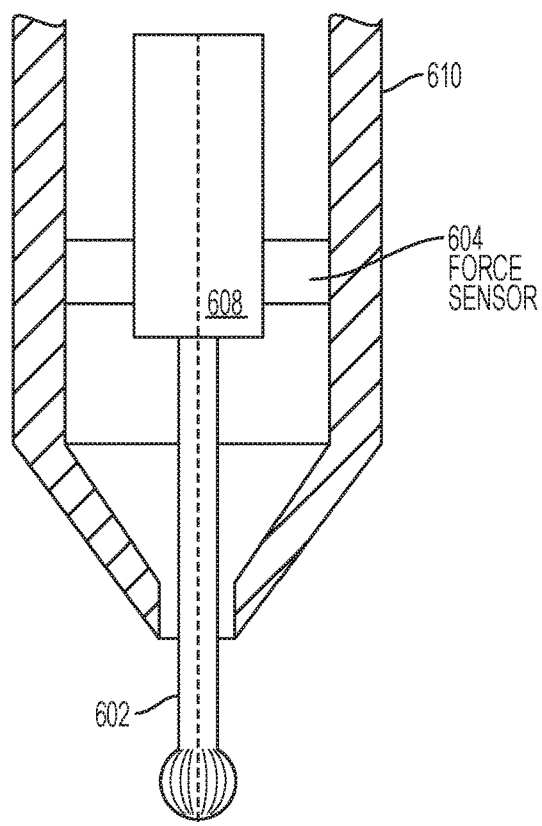
Figure 7D:
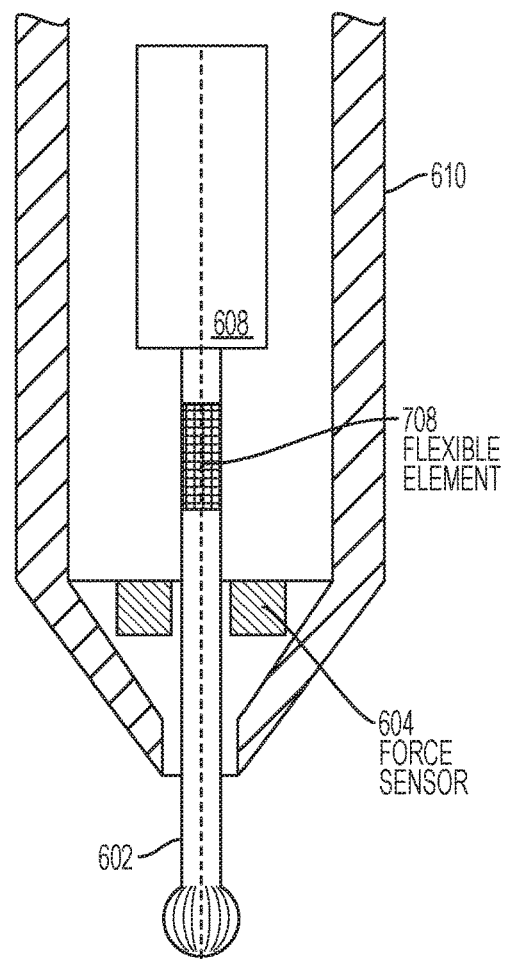

As shown in FIG. 7C, the force sensor 604, in some implementations, measures forces on the motor instead of measuring forces on the drill bit 602 itself. As shown in FIG. 7D, the shaft of the drill bit 602, in some implementations, includes a flexible element 708 that allows the drill bit 602 to bend (e.g., only slightly) such that after deflection of the shaft of the drill bit 602, forces can be measured by the force sensor 604. In some implementations, for the configuration shown in FIGS. 7C and 7D, the measurement of shaft positions (e.g., by sensor 612 as shown in FIG. 6) may be omitted as the forces are measured directly in the instrument coordinate frame.

The tool holder 408 as shown in FIG. 4 may have different implementations. In certain embodiments the tool holder 408 is a flange that a surgical instrument tool may be secured to via, for example, bolts. In some implementations, the tool holder includes a rapid connection mechanism allowing for quick interchange of surgical instruments. In particular it may allow for attaching different surgical instruments/guides necessary for pedicle screw placement as described in U.S. patent application Ser. No. 14/266,769, filed Apr. 30, 2014, and entitled "Apparatus, Systems, and Methods for Precise Guidance of Surgical Tool" and U.S. patent application Ser. No. 14/597,883, filed Jan. 15, 2015, and entitled "Notched Apparatus for Guidance of an Insertable Instrument Along an Axis During Spinal Surgery," both of which are hereby incorporated by reference in their entirety.

Figure 8:
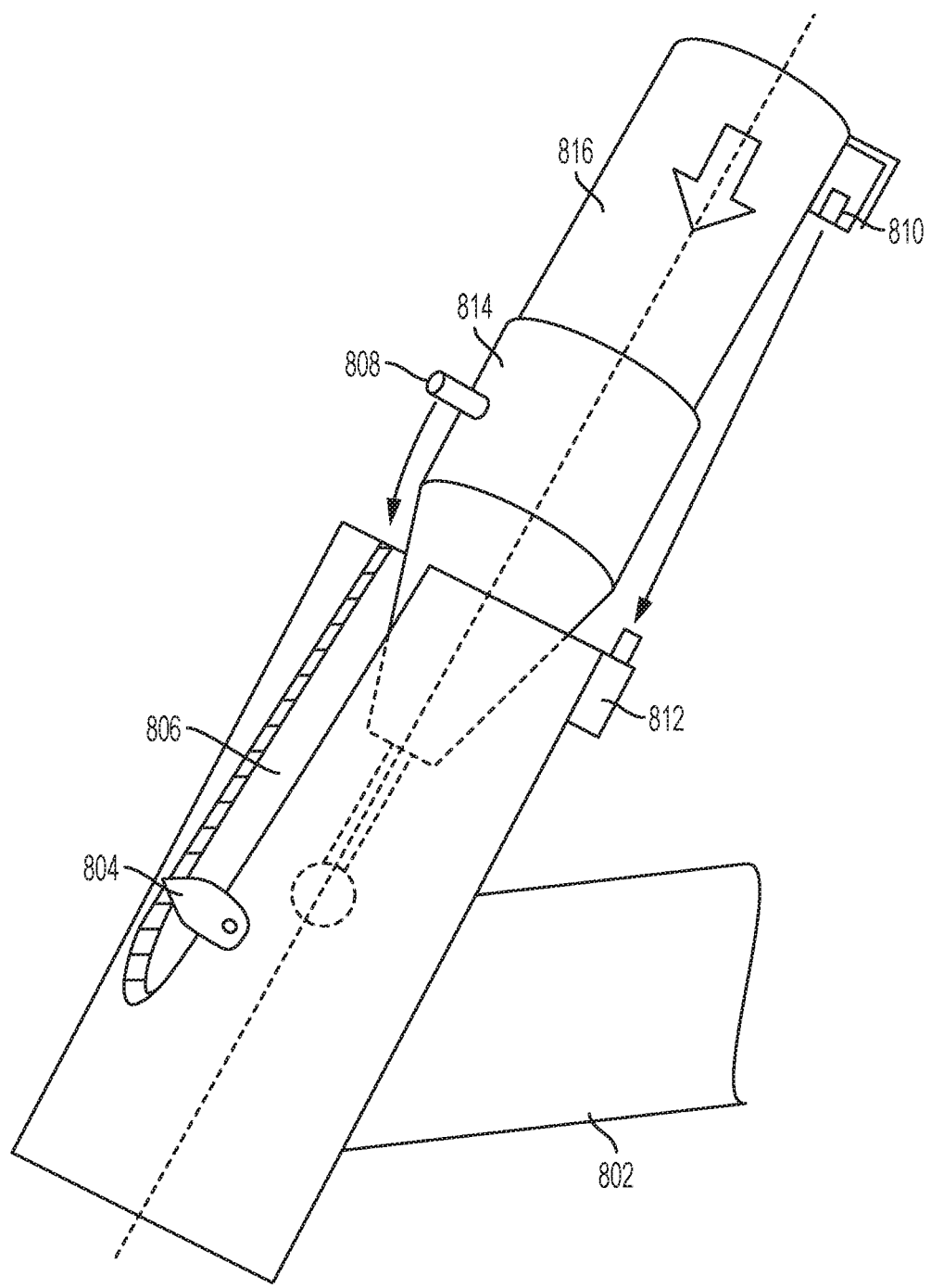
FIG. 8 is an illustration of an example surgical instrument holder.

An example implementation of the tool holder with a rapid connection mechanism is shown in FIG. 8. The tool holder 802 has similar form to the one described in U.S. patent application Ser. No. 14/597,883, filed Mar. 14, 2014, and entitled "Notched Apparatus for Guidance of an Insertable Instrument Along an Axis During Spinal Surgery" a copy of which is included as Appendix B, and is hereby incorporated by reference.

The tubular structure of the tool holder 802, in some implementations, has one or more flanges that are configured for secure coupling of the holder 802 to an end effector of the robotic surgical system. The tubular structure, in some implementations, defines an axis along which movement of a surgical instrument (fitted with a tool support) sliding through the structure is restricted. The tubular structure is configured (e.g., an interior surface of the structure is shaped and sized) to permit a tool support to slide through the holder 802 such that movement of the tool support is constrained to move along the axis (e.g., constrained in all directions except along the axis) defined by the holder 802. Once the surgical instrument with the tool support is fully inserted into the tool holder 802, the surgical instrument 816 can be locked in place using a lock 804. This allows the surgical instrument 816 to be rigidly fixed to the robotic surgical system.

In some implementations, the tool holder 802 has a longitudal notch 806 which is interfaced with peg 808. In some implementations, the peg 808 is a single pin as shown in FIG. 8. In other implementations, the peg 808 supports a navigation tracker such the navigation marker is viewable by a navigation camera along an entire range of movement of the tool support through the holder 802. The navigation marker may be used by navigation camera to track the surgical instrument. The navigation marker may be, for example, navigation tracker such as the Dedicated Nav-Lock™ tracker from Medtronic, Inc. of Minneapolis, Minn. The intra-operative imaging system (not shown) may be, for example, the O-Arm from Medtronic, Inc. of Minneapolis, Minn., the Airo from Mobius Imaging of Ayer, Mass., or the BodyTom® from Neurologica Corp. of Danvers, Mass.

The longitudinal notch 806, in some implementations, is sized in relation to a peg 808. In some implementations, the surgical drill 816 has a sliding surface on the tool support 814 which interface with internal diameter of the holder 802. Sliding surface slides along the interior surface of the holder 802 and permits the tool 816 to slide into the holder such that movement of the tool 816 is constrained in all directions except along the axis defined by the holder 802. The sliding surface 814 is designed in order to slide into the holder 802 allowing the surgeon to achieve a linear motion of the instrument along the holder's 802 axis such that the tool 816 is fixedly attached to the robotic surgical system when fully inserted into the tool holder 802 and the lock 804 is engaged. In some implementations, the sliding surface 814 comprises more than one interface band.

Connectors 810 and 812 can be used to transmit power to the drill 816 and for transmitting information, such as forces measured by a force sensor as described above, between the instrument and the robotic surgical system. The connectors 810 and 812, in some implementations, are positioned such that when the drill 816 is slide completely into the holder 802 the connectors 810 and 812 are electrically engaged.

Several system can be used for attachment of a drill to the robot. In each instance, for example, the following requirements should be met: (i) fixation has high rigidity, (ii) fixation of the instrument shall be done without the need of additional tools, (iii) the external part of the robot-side fixation (flange) shall be easy to clean, and (iv) the instrument-side of the fixation shall be sterilizable in an autoclave.

In certain embodiments, the instrument (e.g., drill) can be secured to the robot using a bolt and pin based fixation system, such as the system described in U.S. patent application Ser. No. 14/695,154, filed Apr. 24, 2015, entitled "Surgical Instrument Holder for Use with a Robotic Surgical System," the contents of which are hereby incorporated by reference in its entirety. In order to use this type of system for rigidly fixing a surgical drill to the robot flange, the part referred to as the instrument holder base 1012 in U.S. patent application Ser. No. 14/695,154 is integrated into the surgical drill. Thus, the drill can slide onto a protruding bolt and be secured by a nut, similar to the instrument holder base described in U.S. patent application Ser. No. 14/695,154.

FIGS. 11A through 11F illustrate an example lever system for securing an instrument to a robot.

Robot flange 1152 is fixed to the robot. It contains the lever system 1102 used to generate fixation force through the lever 1102a. Instrument 1150 is shown as a surgical instrument holder, such as that described in U.S. patent application Ser. No. 14/695,154. However, this can be adapted to other instruments, such as a surgical drill.

Figure 11A:
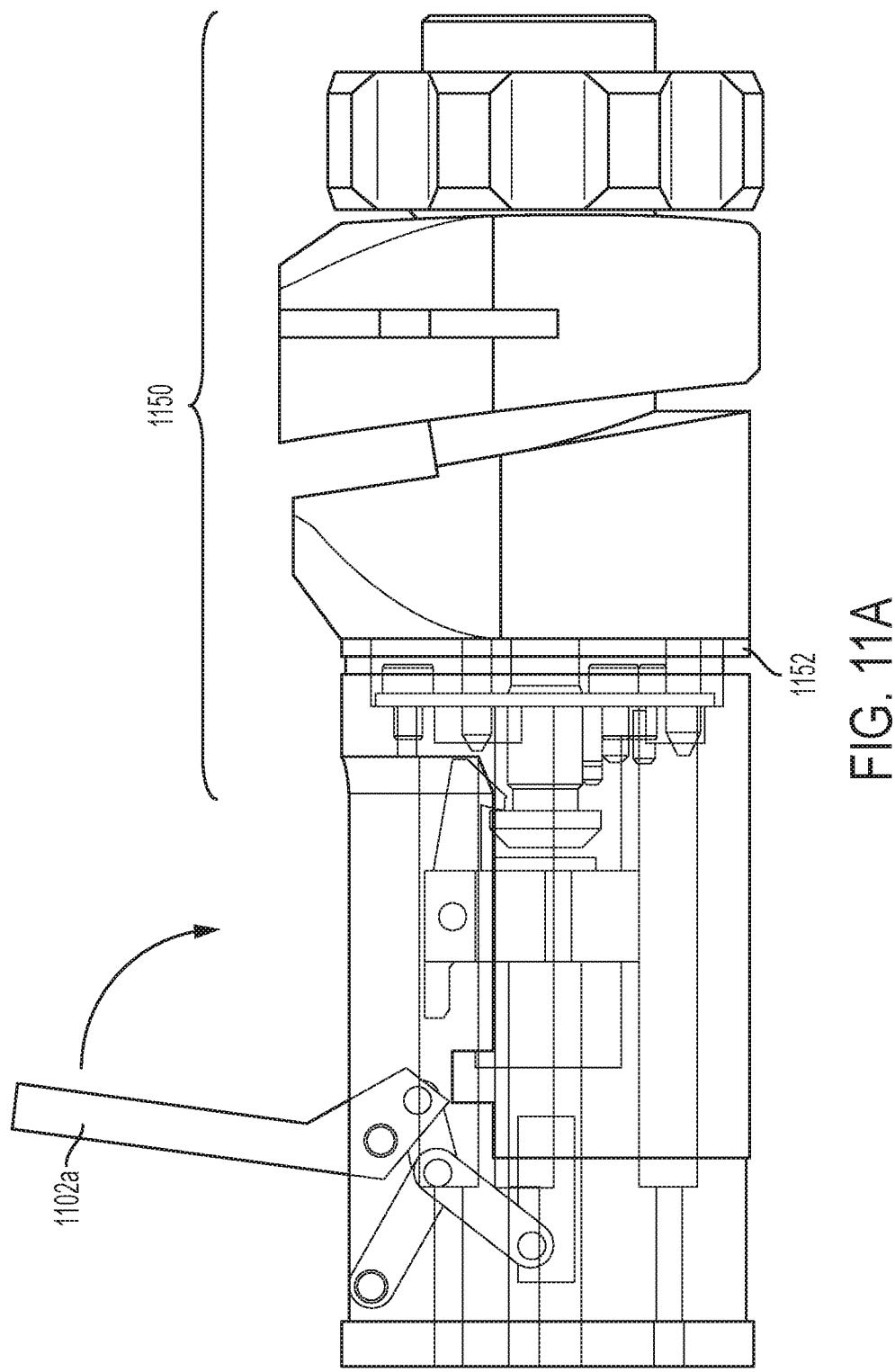
Figure 11C:
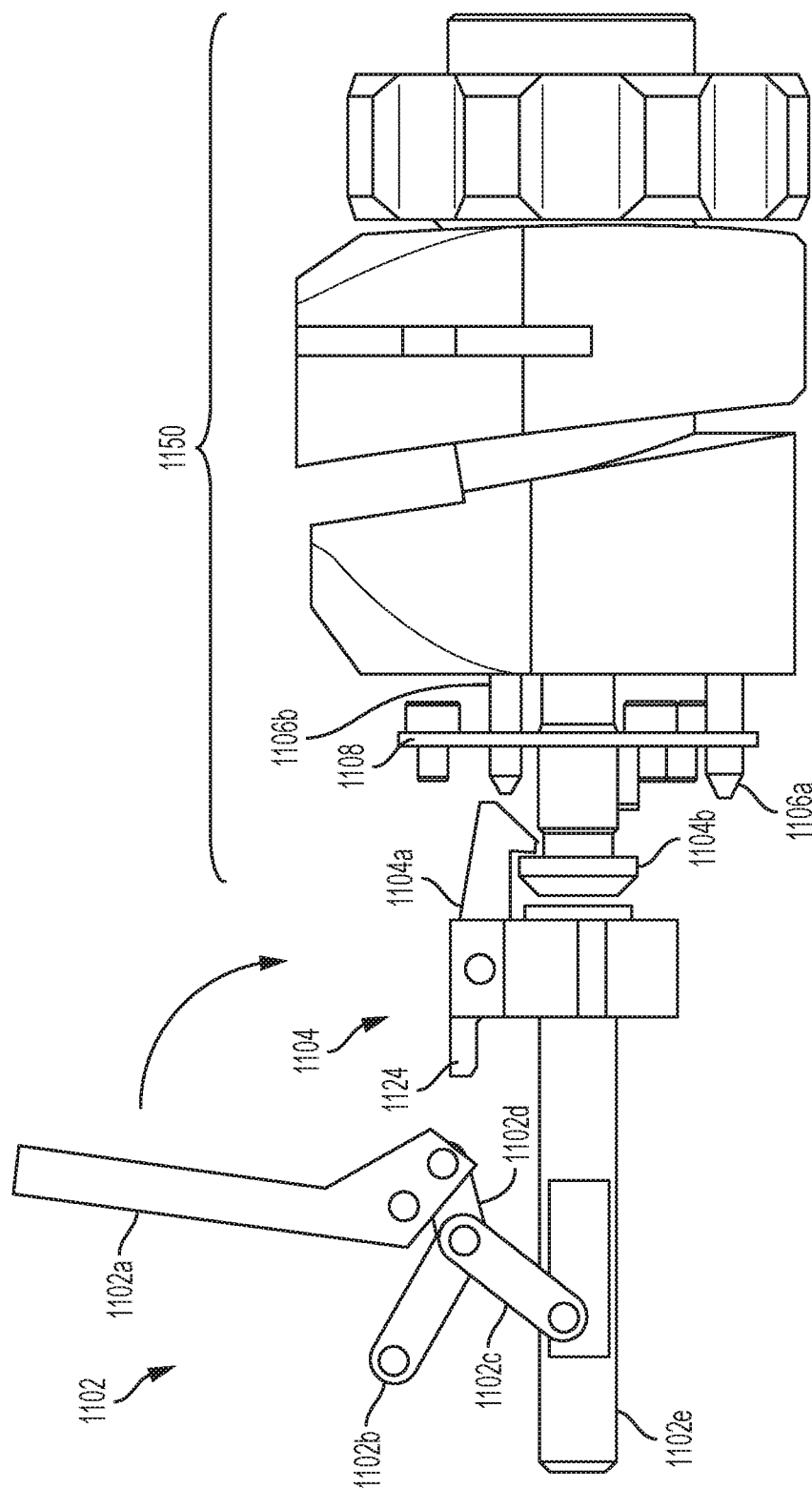

FIG. 11C shows the lever system in more detail. It includes a lever system 1102 (including components 1102a, 1102b, 1102c, and 1102d), quick lock mechanism 1104 (including components 1104a and 1104b) and positioning pins 1106 (including 1106a, 1106b, and 1106c). The lever system 1102 is used to generate high forces. User pushes the lever 1102a in the direction of the arrow. Thanks to the level ratio the forces are increased and transmitted through the intermediate elements (1102b, 1102c, and 1102d) to the rod (1102e). On the rod, the quick lock mechanism 1104 is mounted. It has a quick lock hook 1104a which automatically captures a pin head 1104b which is part of the attached instrument 1150 (e.g., including pins 1106 and pin head 1104b). The guide plate 1108 allows the pin head 1104b to pass therethrough and also allows the positioning pins 1106 (such as those described in U.S. patent application Ser. No. 14/695,154) to interface with the guide plate 1108 to ensure proper alignment of the instrument 1150.

Figure 11D:
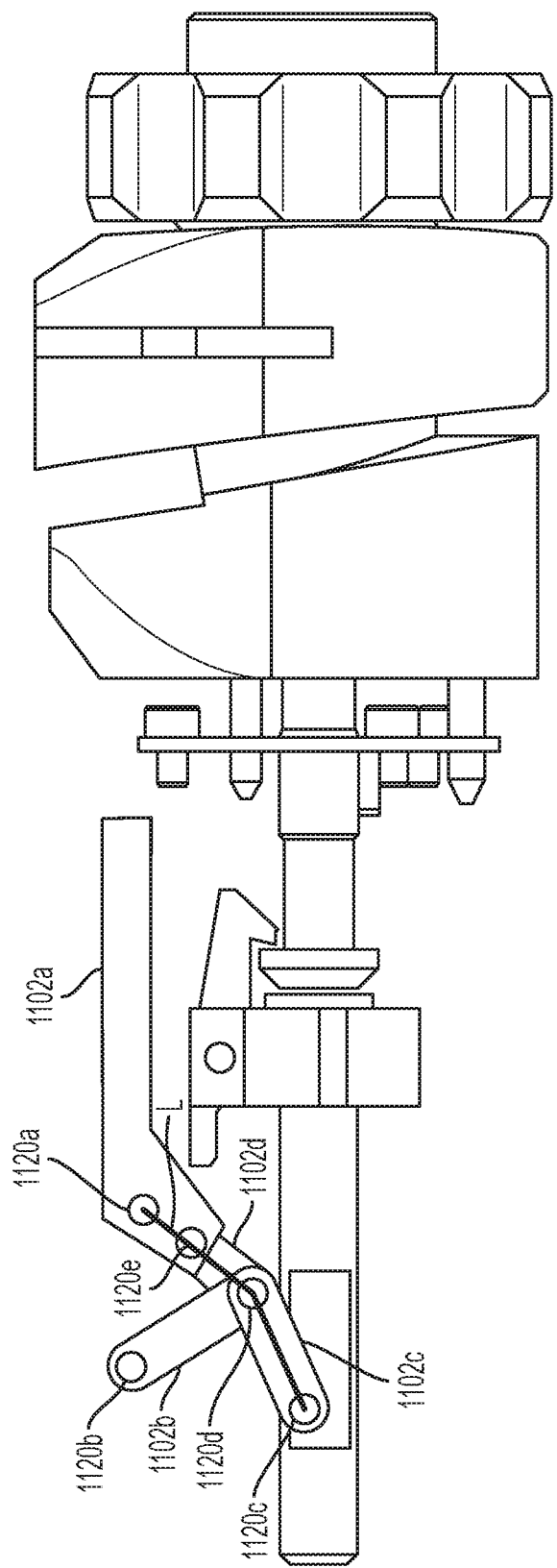
Figure 11E:
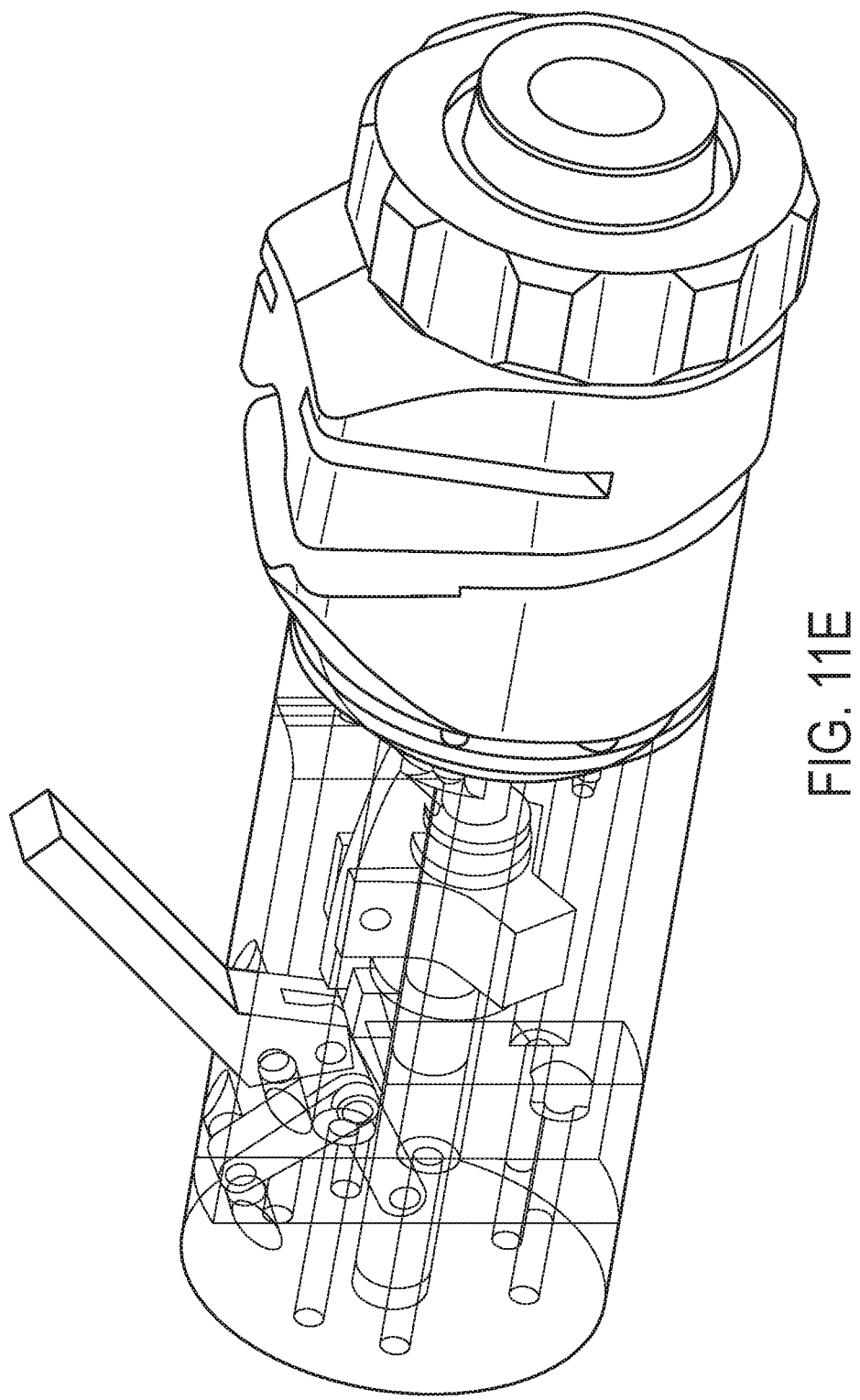
Figure 11F:
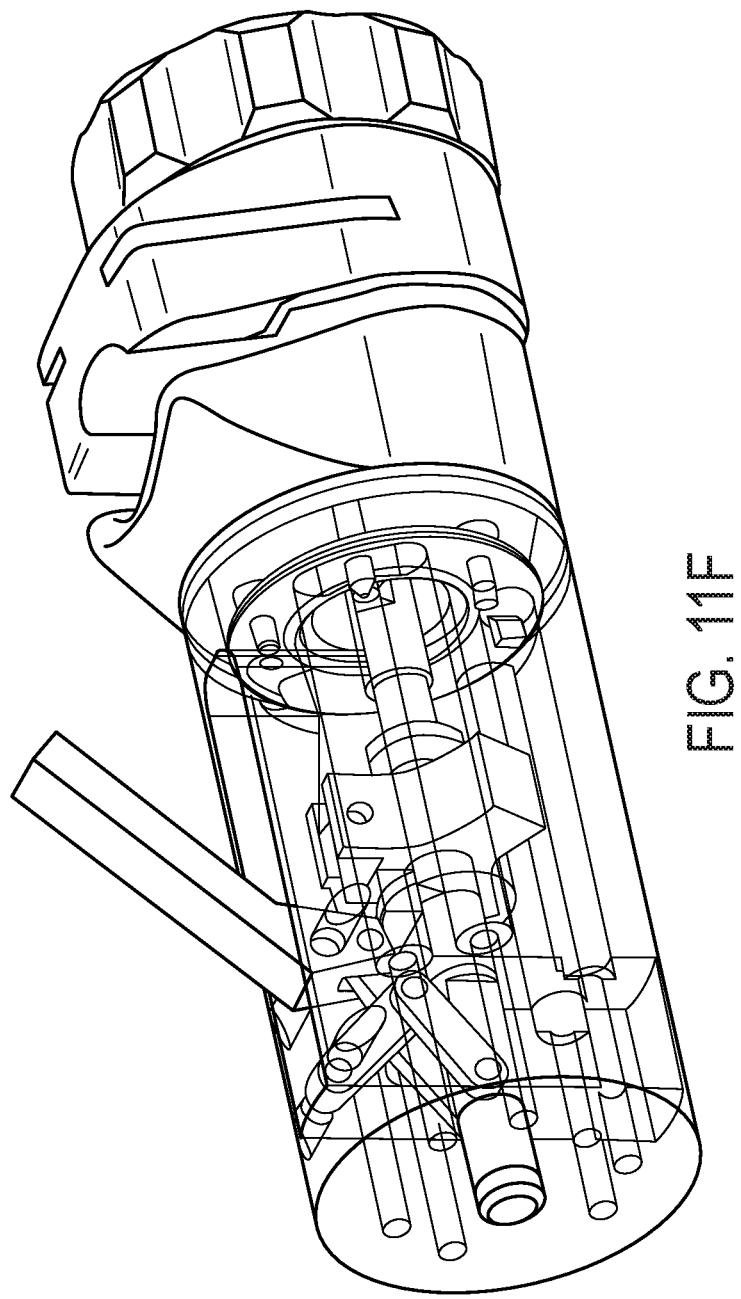

As the lever system 1102 is activated by being pushed in the direction of the arrow, the quick lock mechanism pulls the surgical instrument tight against the flange 1152. The locked position of the mechanism is shown in FIGS. 11B and 11D. When the lever is in the closed position, joint 1120e is on the left side of the line L going through the joints 1120a and 1120c. Thanks to this configuration, a bi-stable behavior is achieved and the lever remains closed until being slightly raised. In this configuration very high forces are achieved because of alignment of intermediate elements 1102c and 1102d (illustrated by the bold line L). This configuration is called a toggle mechanism. In this example, the lever system 1102 is activated by being pushed in the direction of the arrow, element 1102b rotates around pin 1120b, lever 1102a rotates about pin 1120a, element 1102c rotates about pin 1120c, and pin 1120d connects elements 1102b, 1102c, and 1102c. In this example, when the lever 1102a is released, the quick lock hook 1104a can be released (e.g., by pressing tab 1124 directly or indirectly be a separate lever or button) such that the instrument 1150 can be removed. In some embodiments, the linkage is arranged such that the bold line L is straight.

Figure 12:
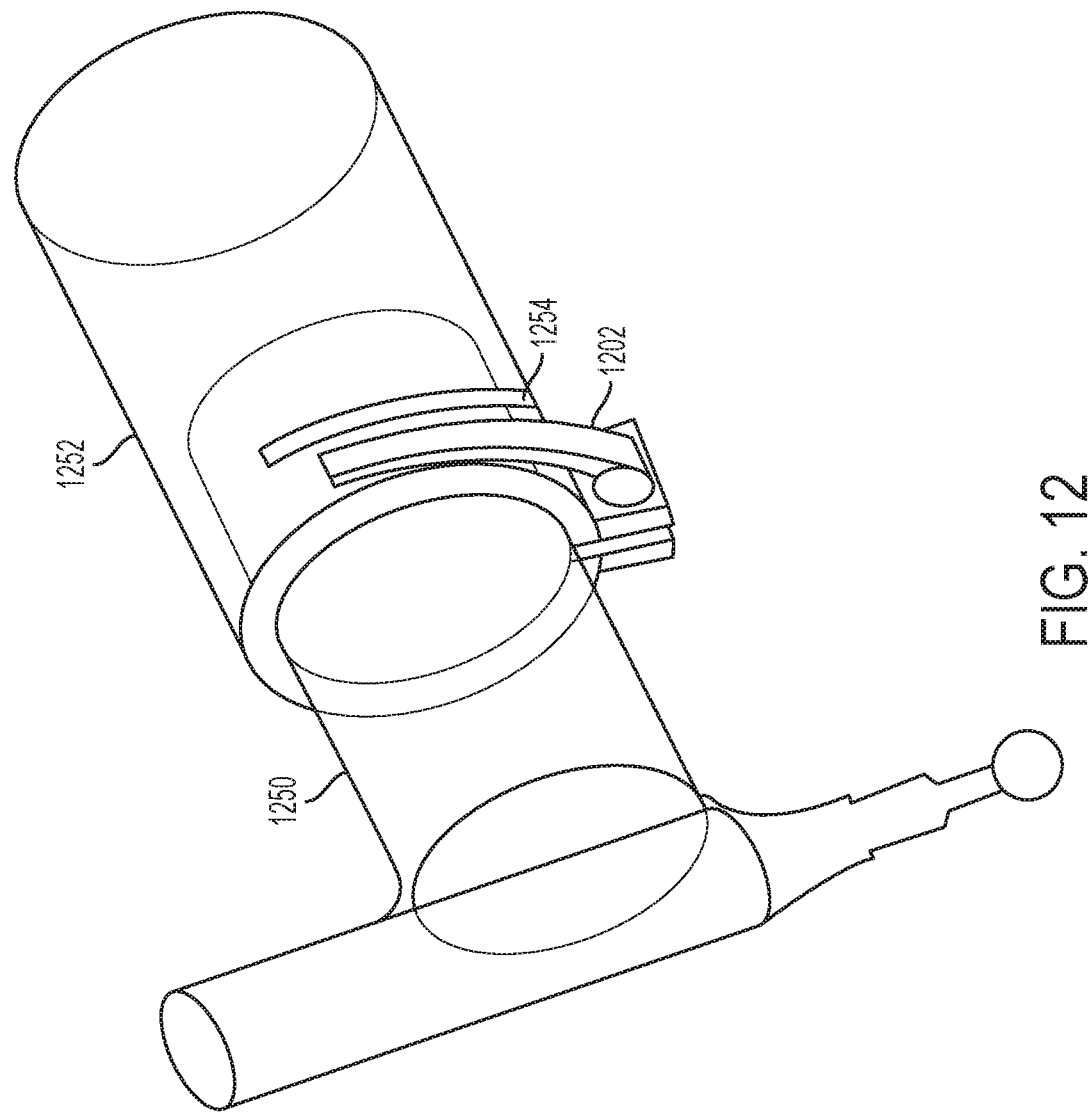
FIG. 12 illustrates an example system for securing an instrument to a robot in accordance with an embodiment of the invention.

FIG. 12 illustrates an example system for securing an instrument to a robot. FIG. 12 illustrates a friction based system. The instrument 1250 is blocked in robot flange 1252 due to the friction between the two parts. The force is applied by the lever 1202 and thanks to the material compliance achieved by adding a notch (grey) the instrument part is tightly blocked inside. It is similar mechanism to the one known in bicycles seats.

Figure 13:
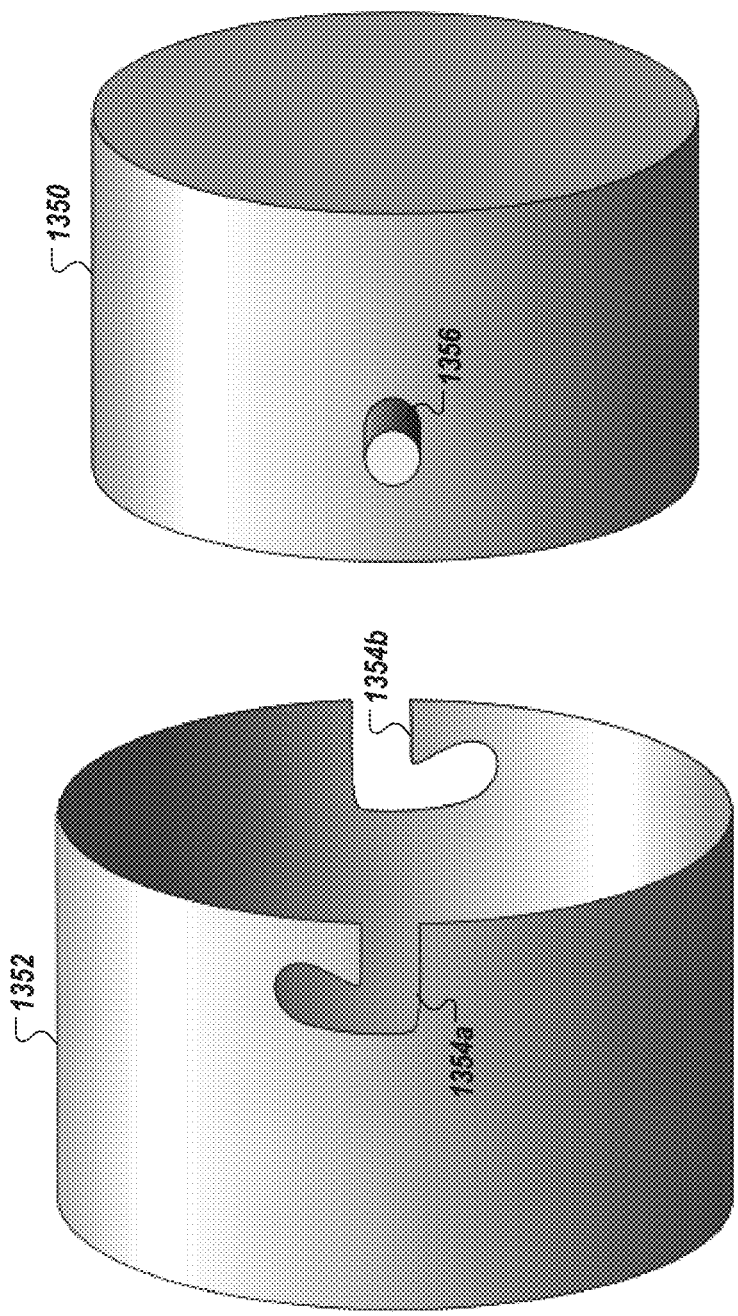
FIG. 13 illustrates an example system for securing an instrument to a robot in accordance with an embodiment of the invention.
Figure 14:
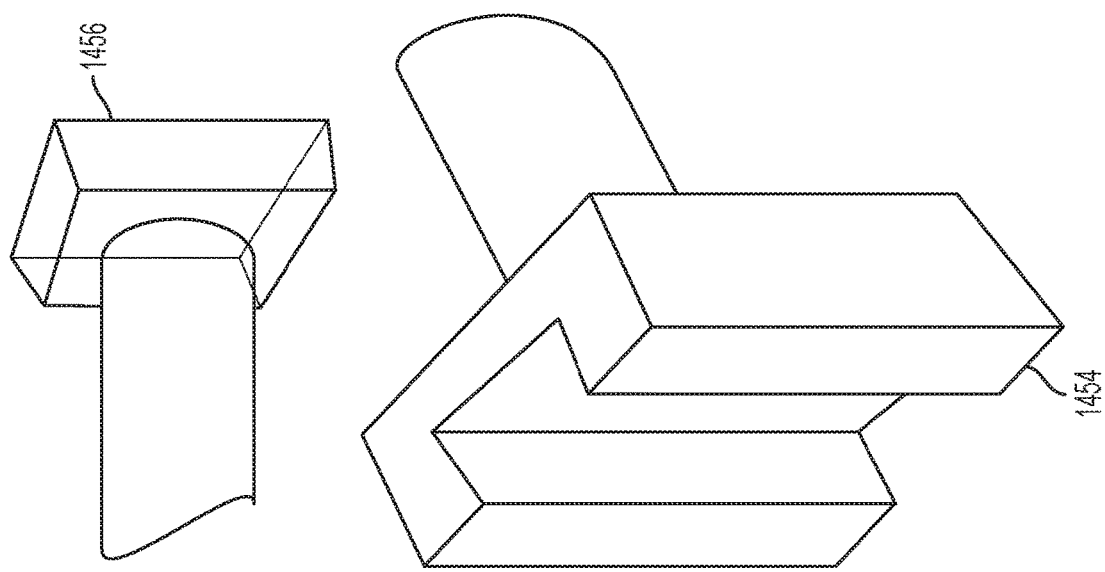
FIG. 14 illustrates an example system for securing an instrument to a robot in accordance with an embodiment of the invention.

FIG. 13 illustrates an example system for securing an instrument to a robot. In this example, a shape lock system is used to secure the instrument to the robot. Shape locks can be achieved between two elements having specific forms. An example is a Bayonet mount shown in this example. The robot flange 1352 includes a pair of shape lock cutouts 1354a and 1354b (two cutouts are shown here, however, more cutouts may be used, such as 4, 5, or 6 cutouts) and the instrument 1350 includes a pair of protrusions 1356 (only one is shown in this illustration). The protrusions 1356 engage the cutouts 1354a and 1354b when the instrument 1350 slides into the flange 1352. The instrument 1350 can be twisted such that is it locked to the flange 1352 by the protrusions 1356 and the cutouts 1354a and 1354b FIG. 14 illustrates an example system for securing an instrument to a robot. Linear guides, such as guide 1454, can be used to lock the instrument in the robot flange. A spring or other device can be used to remove any mechanical backlash such that the instrument cannot be removed after being inserted into the guide until the spring or other mechanism is released. A corresponding member 1456 is attached to the instrument and engages the guide 1454 which is attached to the robot flange.

The disclosed technology, in some implementations, includes a method of performing surgery. Initially, an incision is made and the vertebra is exposed. In some implementations, the frame of the navigation system is attached to the patient in the place selected by the surgeon. Intra-operative medical images of the target anatomy may be obtained. Alternatively, images are acquired pre-operatively. Once the images are obtained, the images must be matched to the actual patient position by a process called registration. For intra-operative images, an automatic algorithm may be used to register the actual patient position with the intra-operative images. Alternatively, point-to-point registration or surface matching may be used. During the surgery, if the surgeon decides to perform fixation of the spine using pedicle screws, he can place them with assistance of the robotic system as described in U.S. patent application Ser. No. 14/266,769, filed Apr. 30, 2014, and entitled "Apparatus, Systems, and Methods for Precise Guidance of Surgical Tool" which is hereby incorporated by reference in its entirety.

Figure 9:
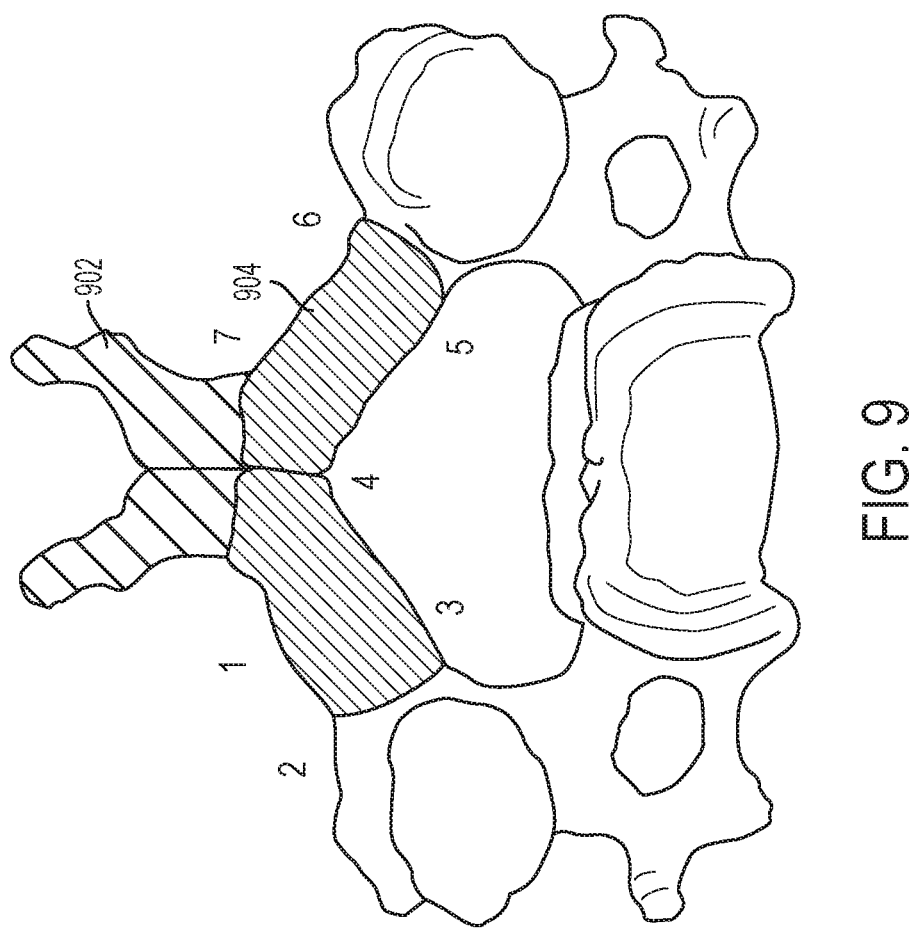
FIG. 9 is an illustration of volumetric planning.

Some surgeries require the surgeon to remove vertebrae volume. The disclosed technology provides an effective and quick way for the surgeon to define volume to be removed. FIG. 9 is an illustration of volumetric planning. In some implementations, volumetric planning is linked with registration precision improvement algorithms. For example, the surgeon may use the navigation system pointer to measure points or follow a path traced by the surgeon using the pointer, thereby generating a set of points that identify (e.g., outline) the volume to be removed. Alternatively, in some implementations, the surgeon uses robot end effector in force control mode (e.g., as described in U.S. patent application Ser. No. 14/266,769, filed Apr. 30, 2014, and entitled "Apparatus, Systems, and Methods for Precise Guidance of Surgical Tool," which is hereby incorporated by reference in its entirety, to identify the points (e.g., the points identifying the volume to be removed). The position of the robot end effector may be tracked by the navigation system using a navigation marker fixed in relation to the surgical instrument Additionally, the volume can be identified using automatic segmentation, semi-automatic segmentation (e.g., using surgeon-defined points or corrections), or fully manual when surgeon/assistant/neurologist defines volume by manually selecting etc. the "pixels"/"voxels" to be removed.

In some implementations, a surgeon first removes the spinous process 902 using, for example, pliers and cutting along the red zigzag line as shown in FIG. 9. Next, the surgeon identifies the extremities of the volume to be removed (shown in blue and labeled as 904. The surgeon can do this by using a navigation pointer and pointing to separate points (e.g. points (1), (2), (3), (4), (5), (6), and (7)) on the patient anatomy or, alternatively, the navigation system may follow a path identified by the surgeon and automatically collect of points. In some implementations, the system generates the volume to be removed by taking a set of points (e.g., identified by the surgeon) and/or patient volumetric information (e.g., medical images) and identifying parts of the vertebrae to be removed. The system, in some implementations, combines the points identified by the surgeon and the patient volumetric information to identify the volume to be removed. In some implementations, the system utilizes medical image segmentation (e.g., statistical shape modeling) to identify the volume. The navigation system may track the points identified by the surgeon and medical images on the navigation screen, in some implementations, are automatically updated to show feedback about the planning. This can be achieved, for example, using different colors on several views of medical images (e.g., the blue section shown in FIG. 9).

The planning algorithms recognize which part of the spinous process was removed. In some implementations, this is achieved if the surgeon shows a point on the patient anatomy which normally should be inside bone. If surgeon is able to point there, it demonstrates that this part of the bone was removed and it should be tagged and shown on a display (e.g., using different color such as red as shown in FIG. 9).

Figure 15:
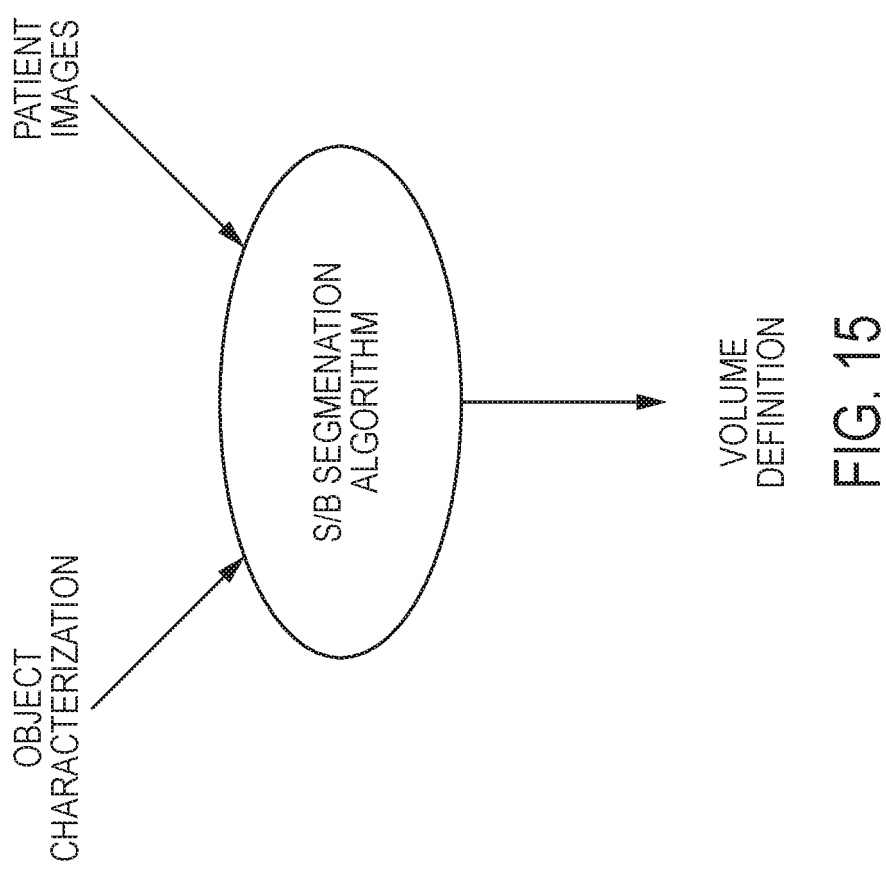
FIG. 15 is an illustration of an example method for volume definition.

In this type of surgery the precision is crucial. Usually after screw placement the relative positions of the vertebrae may change due to forces applied by the surgeon. In order to improve precision points (e.g. points (1), (2), (3), (4), (5), (6), and (7)) on the patient anatomy or a path may be followed to collect a plurality of points that identify the volume to be removed. By matching these points and medical images (e.g. using surface matching algorithms and initial registration as a starting point) an updated, more precise position of the vertebra can be found and used in the next steps of the surgery. In particular, in some implementations, the combination of the points identified by the surgeon and the patient volumetric information (e.g., medical images) allows for a more precise mapping of the volume to be removed. In certain embodiments, these points are collected using the robot in manual or lose control as described in relation to FIG. 9. The force sensor can be used to automatically detect bone versus tissue, something that is difficult to do manually. In certain embodiments, automatic and semi-automatic segmentation algorithms for use van be used to plan a volume to be removed as well as other surgeries. FIG. 15 is an illustration of an example method for volume definition.

Object characterization as shown in FIG. 15 defines the object to be removed. The characterization can be identified spatially, such as set of points delimiting the volume to be removed, or by identifying the type of surgery or volume to remove, e.g. spinous process, lamina, etc. As such, the object characterization can be the set of points identified by the surgeon (e.g., using a pointer) to delineate the area to remove (or operate on in another example), the operation being performed, the specific area to be removed (e.g., identification of a specific portion of the body (e.g., lamina of c7 vertebrae), or a set of the above.

Patient images as shown in FIG. 15 represents the set of images for which the actual volume definition should apply. These images can be CT, MRI, X-ray and/or fluoroscopy images.

The segmentation algorithm takes the object characterization and patient images as an input and gives on the output an exact volume definition which in objective, measurable terms specifying the volume to be removed (e.g. series of spatial coordinates, volume mesh, voxel data etc.). In some implementations, the object characterization is not an input into the algorithm. For example, the patient images and the specific area to be removed (e.g., identification of a specific portion of the body (e.g., lamina of c7 vertebrae) can be the input to the algorithm and the algorithm can determine the area to be removed. In some implementations, the area identified for removal by the algorithm is displayed back to the user (e.g., via a display on the robot) for confirmation by the surgeon.

Good results of the automatic or semi-automatic segmentation in medical domain were obtained using atlas based segmentation, e.g. Expectation-Maximization algorithm or Statistical Shape Modelling algorithm. In Statistical Shape Modelling (SSM) a statistical atlas of the segmented anatomy is created. For example, in the case of the vertebrae lamina, it would require analyzing e.g. 30 representative laminas on medical images and defining a probabilistic representative of the shape called atlas. Once the atlas is generated, its relative position to the patient images and object characterization can be found (this step is called registration). Most often it is defined as a registration matrix. Next, a segmentation algorithm kernel, e.g. Gaussian kernel or multi-scale Gaussian kernel, transforms the atlas to fulfill the constraints of the object definition and patient images. As a result a volume definition is obtained and can be reused in further algorithm steps.

Next, the robot can be automatically brought to the volume or a surgeon may move the robot to the arm using the hands-on control mode as described in U.S. patent application Ser. No. 14/266,769, filed Apr. 30, 2014, and entitled "Apparatus, Systems, and Methods for Precise Guidance of Surgical Tool" which is hereby incorporated by reference in its entirety. The planned volume may be removed using robotic assistance in several ways. In some implementations, the volume may be removed based on stay-in/no-go zones as described in U.S. patent application Ser. No. 14/009,050, filed Jan. 10, 2014, and entitled "Robotic System and Method for Spinal and Other Surgeries" which is hereby incorporated by reference in its entirety. The removing tool stays blocked inside virtual volume (constrained movement) as long as it is not completely removed or the surgeon voluntarily wants to quit the volume.

Figure 10:
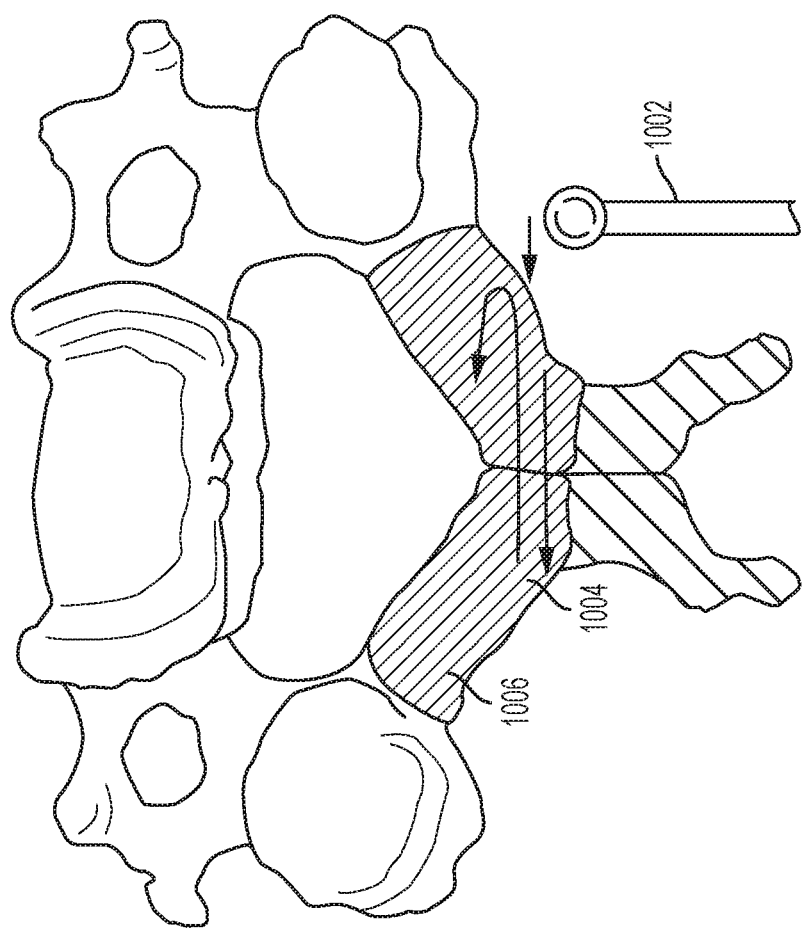
FIG. 10 is an illustration of volume removal.

An alternative approach for removing the appropriate volume is shown in FIG. 10. In this implementation, the robot automatically moves the drilling/milling/erasing instrument 1002 in a type of "painting" trajectory while being supervised by the surgeon. It is important to indicate to user the volume that has be removed 1004 and remaining volume 1006. This may be shown on a display of the robot or on a display separate from the robot.

A surgeon can supervise the robot by looking at the actual position on the navigation screen. The surgeon can stop the robot movement at any time, for example, if the surgeon is concerned about the position of the removal instrument. In some implementations, a dead-man switch is used. The switch may be activated if the surgeon places his/her hands on the tool holder interface or if the surgeon removes his/her hands from the tool holder interface. Alternatively, or in addition, presence detection switches may be used and/or voice recognition may be used to recognize gestures and voice commands, respectively.

During volume removal a force sensor signal can be used to detect if the surgical instrument goes across the edge of the vertebra and, in response, the robotic surgical system can prevent movement of the surgical instrument and destruction of surrounding tissue. This is achieved, for example, using edge detection algorithms which use relative changes in force. Additionally, in some implementations, neuro-monitoring may be used for detection of nervous system infraction.

In some implementations, it is not necessary for a robotic system to completely remove the volume. In the clinical scenario the robot may be used to partially remove the target volume, thereby leaving the most difficult and less laborious parts of the tissue to be removed manually by the surgeon. The amount of the target volume removed by the robot, in some implementations, is controlled during the volume planning phase.

After the robot finishes removing the target volume (e.g., the entire volume or a portion of the volume), the robot is moved away from the patient. In some implementations, this is done automatically by the robot itself. In other implementations, the robotic end effect is manually moved using the hands-on control mode. In some implementations, after moving the robot away the surgeon may inspect the removal of the volume by the robot and/or complete the surgery manually.

Figure 16:
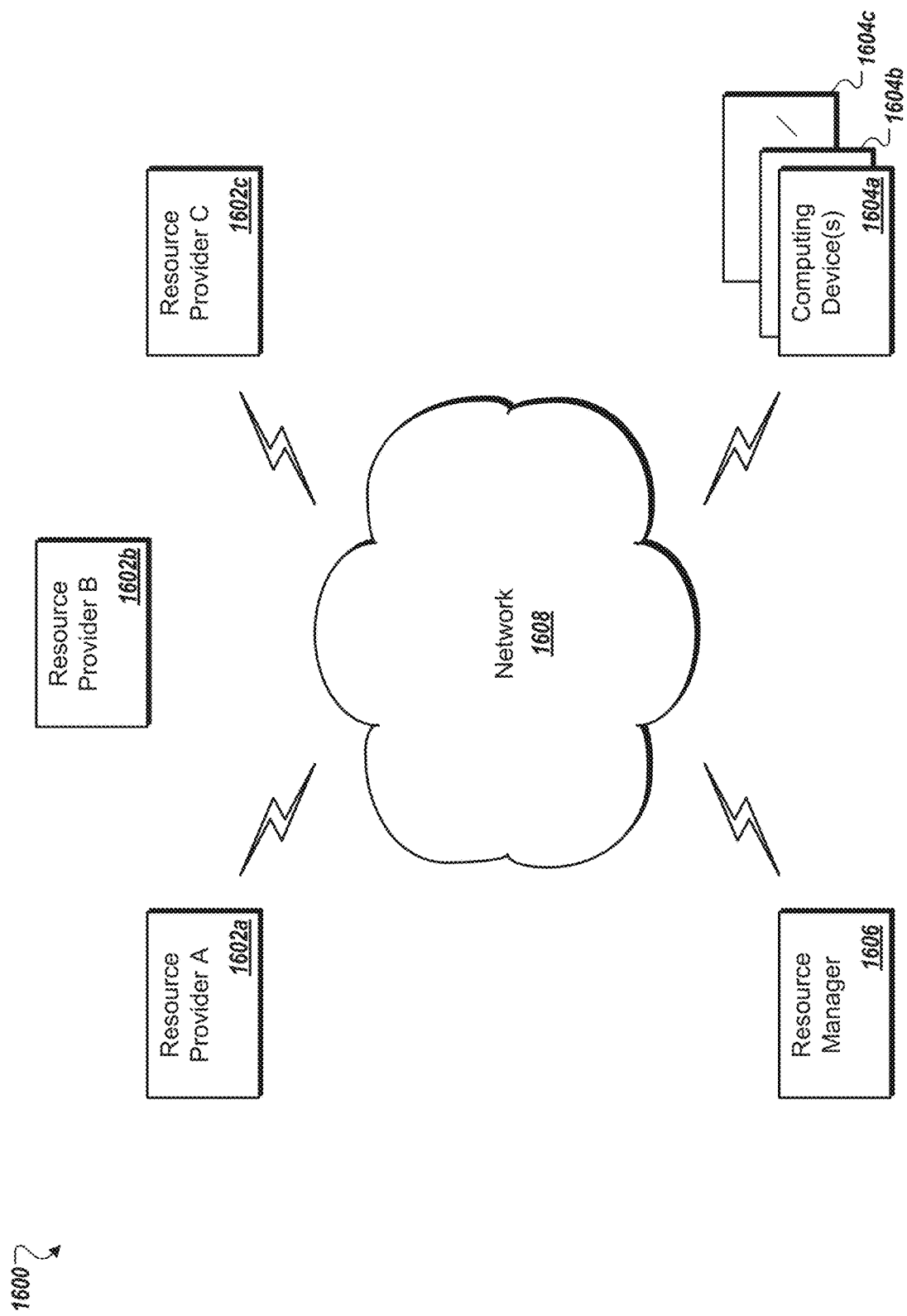
FIG. 16 shows a block diagram of an exemplary cloud computing environment.

As shown in FIG. 16, an implementation of a network environment 1600 for use with the robotic surgical system is shown and described. In brief overview, referring now to FIG. 16, a block diagram of an exemplary cloud computing environment 1600 is shown and described. The cloud computing environment 1600 may include one or more resource providers 1602a, 1602b, 1602c (collectively, 1602). Each resource provider 1602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1602 may be connected to any other resource provider 1602 in the cloud computing environment 1600. In some implementations, the resource providers 1602 may be connected over a computer network 1608. Each resource provider 1602 may be connected to one or more computing device 1604a, 1604b, 1604c (collectively, 1604), over the computer network 1608.

The cloud computing environment 1600 may include a resource manager 1606. The resource manager 1606 may be connected to the resource providers 1602 and the computing devices 1604 over the computer network 1608. In some implementations, the resource manager 1606 may facilitate the provision of computing resources by one or more resource providers 1602 to one or more computing devices 1604. The resource manager 1606 may receive a request for a computing resource from a particular computing device 1604. The resource manager 1606 may identify one or more resource providers 1602 capable of providing the computing resource requested by the computing device 1604. The resource manager 1606 may select a resource provider 1602 to provide the computing resource. The resource manager 1606 may facilitate a connection between the resource provider 1602 and a particular computing device 1604. In some implementations, the resource manager 1606 may establish a connection between a particular resource provider 1602 and a particular computing device 1604. In some implementations, the resource manager 1606 may redirect a particular computing device 1604 to a particular resource provider 1602 with the requested computing resource.

Figure 17:
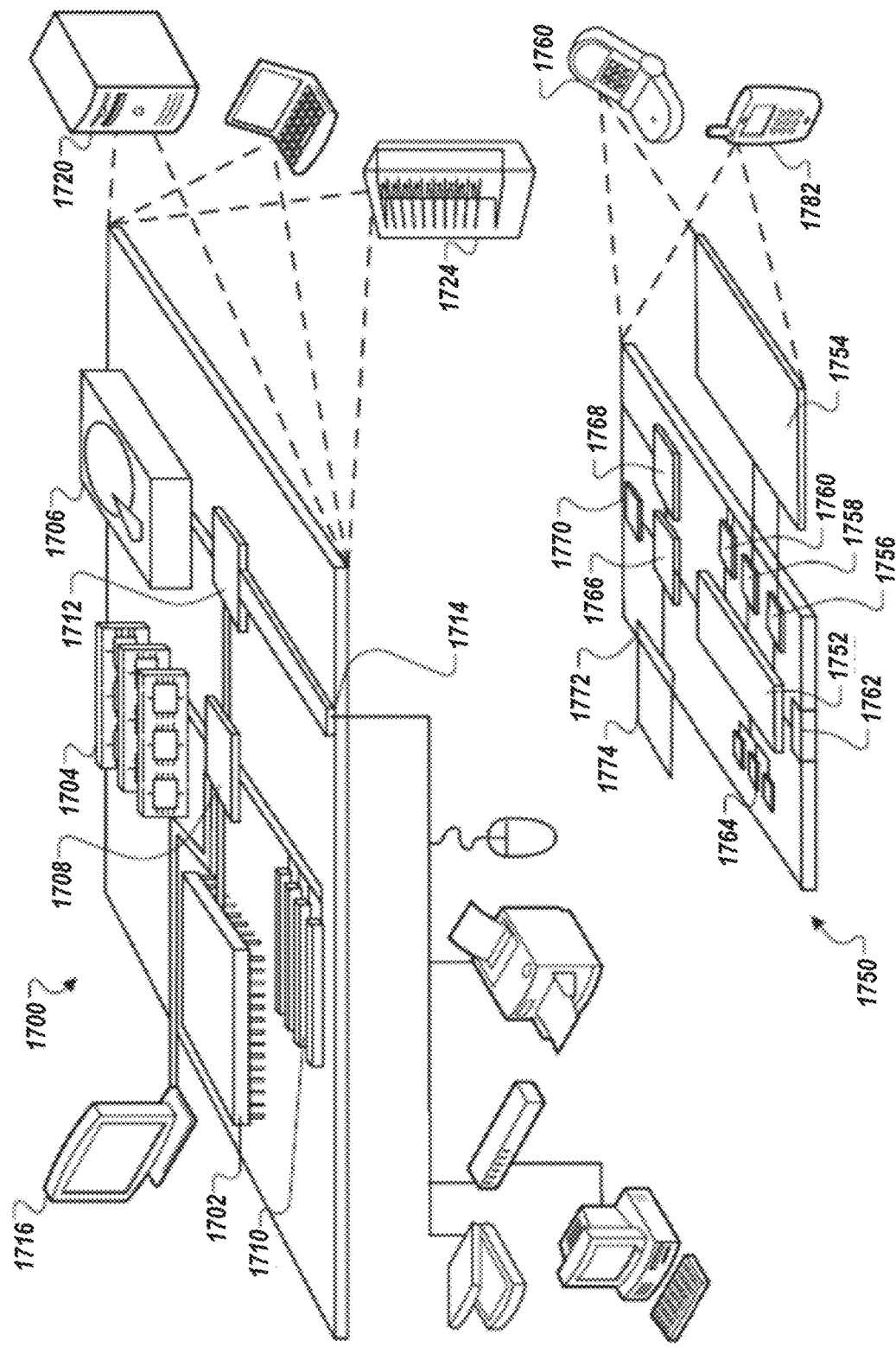
FIG. 17 is a block diagram of a computing device and a mobile computing device.

FIG. 17 shows an example of a computing device 1700 and a mobile computing device 1750 that can be used to implement the techniques described in this disclosure. The computing device 1700 is intended to represent various forms of digital computers, such as laptops, desktops, workstations, personal digital assistants, servers, blade servers, mainframes, and other appropriate computers. The mobile computing device 1750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1700 includes a processor 1702, a memory 1704, a storage device 1706, a high-speed interface 1708 connecting to the memory 1704 and multiple high-speed expansion ports 1710, and a low-speed interface 1712 connecting to a low-speed expansion port 1714 and the storage device 1706. Each of the processor 1702, the memory 1704, the storage device 1706, the high-speed interface 1708, the high-speed expansion ports 1710, and the low-speed interface 1712, are interconnected using various busses, and may be mounted on a common motherboard or in other manners as appropriate. The processor 1702 can process instructions for execution within the computing device 1700, including instructions stored in the memory 1704 or on the storage device 1706 to display graphical information for a GUI on an external input/output device, such as a display 1716 coupled to the high-speed interface 1708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1704 stores information within the computing device 1700. In some implementations, the memory 1704 is a volatile memory unit or units. In some implementations, the memory 1704 is a non-volatile memory unit or units. The memory 1704 may also be another form of computer-readable medium, such as a magnetic or optical disk.

The storage device 1706 is capable of providing mass storage for the computing device 1700. In some implementations, the storage device 1706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1702), perform one or more methods, such as those described above. The instructions can also be stored by one or more storage devices such as computer- or machine-readable mediums (for example, the memory 1704, the storage device 1706, or memory on the processor 1702).

The high-speed interface 1708 manages bandwidth-intensive operations for the computing device 1700, while the low-speed interface 1712 manages lower bandwidth-intensive operations. Such allocation of functions is an example only. In some implementations, the high-speed interface 1708 is coupled to the memory 1704, the display 1716 (e.g., through a graphics processor or accelerator), and to the high-speed expansion ports 1710, which may accept various expansion cards (not shown). In the implementation, the low-speed interface 1712 is coupled to the storage device 1706 and the low-speed expansion port 1714. The low-speed expansion port 1714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1700 may be implemented in a number of different forms, as shown in the figure. For example, it may be implemented as a standard server 1720, or multiple times in a group of such servers. In addition, it may be implemented in a personal computer such as a laptop computer 1722. It may also be implemented as part of a rack server system 1724. Alternatively, components from the computing device 1700 may be combined with other components in a mobile device (not shown), such as a mobile computing device 1750. Each of such devices may contain one or more of the computing device 1700 and the mobile computing device 1750, and an entire system may be made up of multiple computing devices communicating with each other.

The mobile computing device 1750 includes a processor 1752, a memory 1764, an input/output device such as a display 1754, a communication interface 1766, and a transceiver 1768, among other components. The mobile computing device 1750 may also be provided with a storage device, such as a micro-drive or other device, to provide additional storage. Each of the processor 1752, the memory 1764, the display 1754, the communication interface 1766, and the transceiver 1768, are interconnected using various buses, and several of the components may be mounted on a common motherboard or in other manners as appropriate.

The processor 1752 can execute instructions within the mobile computing device 1750, including instructions stored in the memory 1764. The processor 1752 may be implemented as a chipset of chips that include separate and multiple analog and digital processors. The processor 1752 may provide, for example, for coordination of the other components of the mobile computing device 1750, such as control of user interfaces, applications run by the mobile computing device 1750, and wireless communication by the mobile computing device 1750.

The processor 1752 may communicate with a user through a control interface 1758 and a display interface 1756 coupled to the display 1754. The display 1754 may be, for example, a TFT (Thin-Film-Transistor Liquid Crystal Display) display or an OLED (Organic Light Emitting Diode) display, or other appropriate display technology. The display interface 1756 may comprise appropriate circuitry for driving the display 1754 to present graphical and other information to a user. The control interface 1758 may receive commands from a user and convert them for submission to the processor 1752. In addition, an external interface 1762 may provide communication with the processor 1752, so as to enable near area communication of the mobile computing device 1750 with other devices. The external interface 1762 may provide, for example, for wired communication in some implementations, or for wireless communication in other implementations, and multiple interfaces may also be used.

The memory 1764 stores information within the mobile computing device 1750. The memory 1764 can be implemented as one or more of a computer-readable medium or media, a volatile memory unit or units, or a non-volatile memory unit or units. An expansion memory 1774 may also be provided and connected to the mobile computing device 1750 through an expansion interface 1772, which may include, for example, a SIMM (Single In Line Memory Module) card interface. The expansion memory 1774 may provide extra storage space for the mobile computing device 1750, or may also store applications or other information for the mobile computing device 1750. Specifically, the expansion memory 1774 may include instructions to carry out or supplement the processes described above, and may include secure information also. Thus, for example, the expansion memory 1774 may be provide as a security module for the mobile computing device 1750, and may be programmed with instructions that permit secure use of the mobile computing device 1750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1752), perform one or more methods, such as those described above. The instructions can also be stored by one or more storage devices, such as one or more computer- or machine-readable mediums (for example, the memory 1764, the expansion memory 1774, or memory on the processor 1752). In some implementations, the instructions can be received in a propagated signal, for example, over the transceiver 1768 or the external interface 1762.

The mobile computing device 1750 may communicate wirelessly through the communication interface 1766, which may include digital signal processing circuitry where necessary. The communication interface 1766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1768 using a radio-frequency. In addition, short-range communication may occur, such as using a Bluetooth®, Wi-Fi™, or other such transceiver (not shown). In addition, a GPS (Global Positioning System) receiver module 1770 may provide additional navigation- and location-related wireless data to the mobile computing device 1750, which may be used as appropriate by applications running on the mobile computing device 1750.

The mobile computing device 1750 may also communicate audibly using an audio codec 1760, which may receive spoken information from a user and convert it to usable digital information. The audio codec 1760 may likewise generate audible sound for a user, such as through a speaker, e.g., in a handset of the mobile computing device 1750. Such sound may include sound from voice telephone calls, may include recorded sound (e.g., voice messages, music files, etc.) and may also include sound generated by applications operating on the mobile computing device 1750.

The mobile computing device 1750 may be implemented in a number of different forms, as shown in the figure. For example, it may be implemented as a cellular telephone 1780. It may also be implemented as part of a smart-phone 1782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed:

1. A surgical instrument holder for use with a robotic surgical system, the surgical instrument holder comprising:
   a rigid hollow tubular structure adapted to be securely attached to an end effector of a robotic arm, the tubular structure having a proximal open end and a distal open end, the tubular structure defining a longitudinal axis along which movement of a surgical instrument sliding through the tubular structure is restricted, wherein the tubular structure has an interior surface shaped and sized to accommodate the surgical instrument sliding through the tubular structure such that the surgical instrument is constrained to move linearly only along the longitudinal axis defined by the tubular structure; and a connector element attached to the tubular structure that, when engaged with a corresponding connector element associated with the surgical instrument, provides electrical power to a motor included in the surgical instrument;

wherein the tubular structure comprises a longitudinal notch along the length of the tubular structure, wherein the longitudinal notch is sized to fit a peg on the surgical instrument to permit the surgical instrument to slide along the longitudinal axis defined by the tubular structure and to prevent rotation of the surgical instrument about the longitudinal axis of the tubular structure;

wherein the longitudinal notch and the connector element attached to the tubular structure are disposed in predetermined locations such that when the surgical instrument slides completely into the tubular structure, the connector element associated with the surgical instrument is electrically engaged with the connector element attached to the tubular structure.

2. The surgical instrument holder of a claim 1, wherein the tubular structure has an exterior surface comprising at least one flange that is sized and shaped to secure coupling of the surgical instrument holder to an end effector of the robotic surgical system.

3. The surgical instrument holder of claim 1, comprising a lock that, when engaged, restricts movement of the surgical instrument within the rigid hollow tubular structure.

4. The surgical instrument holder of claim 3, wherein the lock, when engaged, prevents removal of the surgical instrument from the tubular structure.

5. The surgical instrument holder of claim 1, comprising a force sensor that measures one or more forces or torques applied to at least a portion of the surgical instrument.

6. The surgical instrument holder of claim 1, wherein: the surgical instrument comprises a force sensor that measures one or more forces or torques applied to at least a portion of the surgical instrument, and the measurement information provided to the surgical instrument holder via the connector element comprises the one or more forces or torques.

7. The surgical instrument holder of claim 1, wherein the longitudinal notch is a slot.

8. The surgical instrument holder of claim 1, wherein the longitudinal notch is sized in relation to the peg to (i) permit a navigation marker attached to the surgical instrument at least in part via the peg to be viewable by a navigation camera along an entire range of movement of the surgical instrument through the tubular structure, and (ii) constrain movement of the marker in a fixed orientation along the axis defined by the tubular structure.

9. The surgical instrument holder of claim 1, wherein the tubular structure has an interior surface sized and shaped to accommodate a tool support of the surgical instrument.

10. The surgical instrument holder of claim 1, comprising a second connector associated with the tubular structure and adapted to communicate with a sensor measuring the position of the surgical instrument.

11. The surgical instrument holder of claim 10, wherein the second connector includes one or more brushes.

12. The surgical instrument holder of claim 1, wherein the rigid hollow tubular structure is a cylindrical structure.

13. A surgical instrument holder for use with a robotic surgical system, the surgical instrument holder comprising:
a rigid hollow tubular structure having a proximal open end and a distal open end, the tubular structure defining a longitudinal axis along which movement of a tool support attached to a surgical instrument sliding through the tubular structure is restricted,
a peg extending from a tool support of the surgical instrument,
wherein the tubular structure has an interior surface shaped and sized to accommodate the surgical instrument sliding through the tubular structure such that the tool support is constrained to move linearly only along the longitudinal axis defined by the tubular structure,
wherein the tubular structure has an exterior surface including at least one flange that is sized and shaped to securely couple the tubular structure to an end effector of the robotic surgical system, and
wherein the tubular structure includes a longitudinal notch along its length, wherein the longitudinal notch is sized to fit the peg on the tool support of the surgical instrument, the peg adapted and sized to permit the tool support to slide along the longitudinal axis defined by the tubular structure, and prevent rotational movement relative to the tubular structure;
a lock that, when engaged, restricts movement of the surgical instrument within the rigid hollow tubular structure; and
a connector element attached to the tubular structure that, when engaged with a corresponding connector element associated with the surgical instrument, provides electrical power to the surgical instrument;
wherein the longitudinal notch and the connector element attached to the tubular structure are disposed in predetermined locations such that when the tool support of the surgical instrument slides completely into the tubular structure, the connector element associated with the surgical instrument is electrically engaged with the connector element attached to the tubular structure.

14. The surgical instrument holder of claim 13, wherein the surgical instrument comprises a force sensor for measuring one or more forces or torques applied to at least a portion of the surgical instrument.

15. The surgical instrument holder of claim 13, wherein the longitudinal notch is a slot.

16. The surgical instrument holder of claim 13, wherein the longitudinal notch is sized in relation to a peg to (i) permit a navigation marker attached to the surgical instrument via the peg to be viewable by a navigation camera along an entire range of movement of the surgical instrument through the tubular structure, and (ii) constrain movement of the marker in a fixed orientation along the axis defined by the tubular structure.

17. The surgical instrument holder of claim 13, comprising a second connector associated with the tubular structure for communicating with a sensor measuring a position of the surgical instrument.

18. The surgical instrument holder of claim 17, wherein the second connector includes one or more brushes.

19. The surgical instrument holder of claim 13, wherein the lock, when engaged, prevents removal of the surgical instrument from the tubular structure.

* * * * *